United States Patent
Hunt et al.

(12)

(10) Patent No.: US 6,340,574 B1
(45) Date of Patent: Jan. 22, 2002

(54) REGULATED AUTOCRINE GROWTH OF MAMMALIAN CELLS

(75) Inventors: Sybille Marie Hunt, Epping; Peter Philip Gray, Edgecliff; Merilyn Joy Sleigh, Neutral Bay, all of (AU)

(73) Assignees: Unisearch Limited, Kensington NSW; Commonwealth Scientific and Industrial Research Organization, Campbell, both of (AU)

( * ) Notice: Subject to any disclaimer, the term of this patent is extended or adjusted under 35 U.S.C. 154(b) by 0 days.

(21) Appl. No.: 09/000,442

(22) PCT Filed: Jul. 26, 1996

(86) PCT No.: PCT/AU96/00472

§ 371 Date: May 19, 1998

§ 102(e) Date: May 19, 1998

(87) PCT Pub. No.: WO97/05240

PCT Pub. Date: Feb. 13, 1997

(30) Foreign Application Priority Data

Jul. 26, 1995 (AU) ............................................ PN4422

(51) Int. Cl.[7] .............................................. C12N 15/00
(52) U.S. Cl. ..................... 435/69.1; 435/375; 435/69.7; 435/70.1; 435/91.4; 435/325; 435/320.1; 435/358; 435/363
(58) Field of Search ............................... 435/325, 358, 435/363, 320.1, 69.1, 375, 69.7, 91.4, 70.1

(56) References Cited

U.S. PATENT DOCUMENTS 5,262,308 A   11/1993   Baserga ..................... 435/69.1

5,723,333 A * 3/1998 Levine ....................... 435/325

FOREIGN PATENT DOCUMENTS

| WO | WO 9103554 | 3/1991 |
| WO | WO 9311247 | 6/1993 |

OTHER PUBLICATIONS

Tohyama et al, *Journal of Experimental Medicine*, 171:389–400 (1990).

Dai et al, *Endocrinology*, 130(6):3175–3183 (1992).

Keith et al, *British Journal of Cancer*, 62(2):388–394 (1990).

Yamada et al, *The EMBO Journal*, 6(9):2705–2709 (1987).

Hapel et al, *Lymphokine Research*, 5(4):249–254 (1986).

Wong et al, *Genes & Development*, 1:358–365 (1987).

Blankenstein et al, *European Journal of Immunology*, 20:2699–2705 (1990).

* cited by examiner

*Primary Examiner*—Lorraine Spector
*Assistant Examiner*—Eliane Lazar-Wesley
(74) *Attorney, Agent, or Firm*—Sughrue Mion, PLLC

(57) ABSTRACT

Methods of production of desired recombinant proteins, polypeptides and peptides are disclosed which utilize mammalian host cells engineered for autonomous and regulated growth in low cost protein/serum-free culture media. Preferred host cells express insulin or an insulin-like growth factor, and/or transferrin and are engineered so that addition of an inducer (e.g., $ZnCl_2+CdCl_2$) halts growth and simultaneously induces the expression of the desired recombinant protein, polypeptide or peptide.

11 Claims, 19 Drawing Sheets

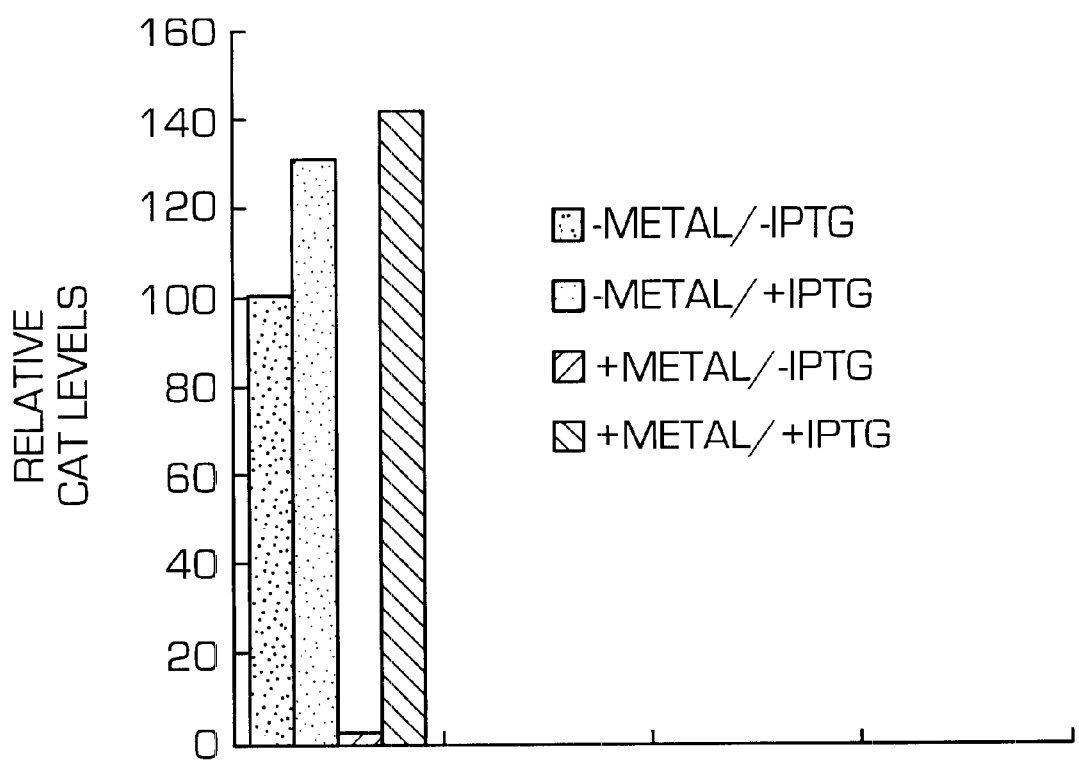

A

|  | Bulk #2 | | clone #1-19 | |
|---|---|---|---|---|
| metal | − | + | − | + |

Tf

B

| metal | − | − | + | + |
|---|---|---|---|---|
| IPTG | − | + | − | + |

2 bulk ——— Tf

1-19 ——— Tf

C

| clones | 25 | | 26 | | 27 | | 28 | | 29 | | 30 | |
|---|---|---|---|---|---|---|---|---|---|---|---|---|
| IPTG | − | + | − | + | − | + | − | + | − | + | − | + |

Tf

| clones | 31 | | 32 | | 33 | | 34 | | 35 | | 36 | |
|---|---|---|---|---|---|---|---|---|---|---|---|---|
| IPTG | − | + | − | + | − | + | − | + | − | + | − | + |

Tf

D

| clone35 | 1 | 2 | 10 µl | | | | | |
|---|---|---|---|---|---|---|---|---|
| metal | − | − | − | − | + | + | ++ | ++ |
| IPTG | − | − | − | + | − | + | − | + |

Tf

| clone36 | 1 | 2 | 10 µl | | | | | |
|---|---|---|---|---|---|---|---|---|
| metal | − | − | − | − | + | + | ++ | ++ |
| IPTG | − | − | − | + | − | + | − | + |

FIGURE 8
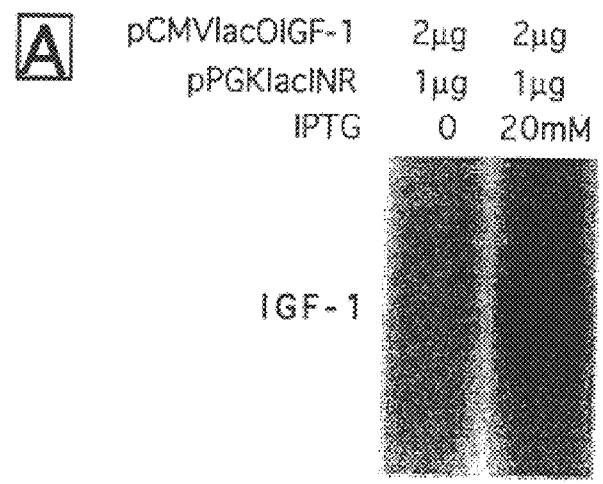
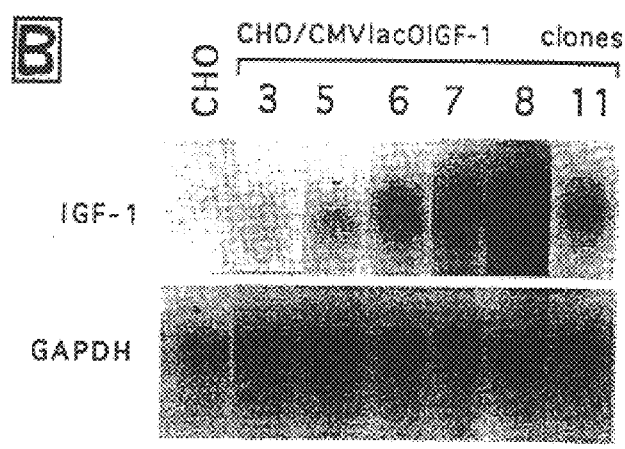
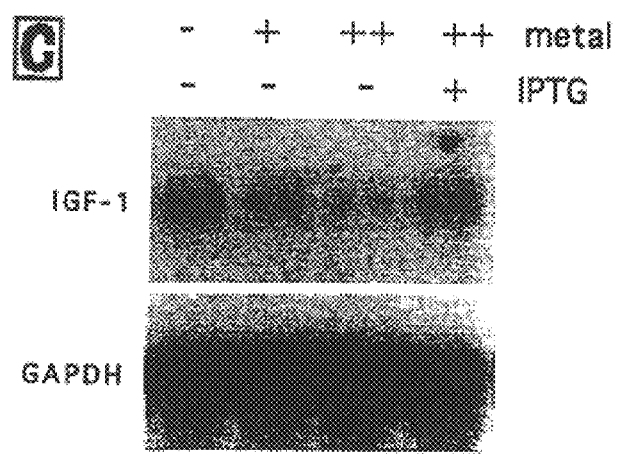

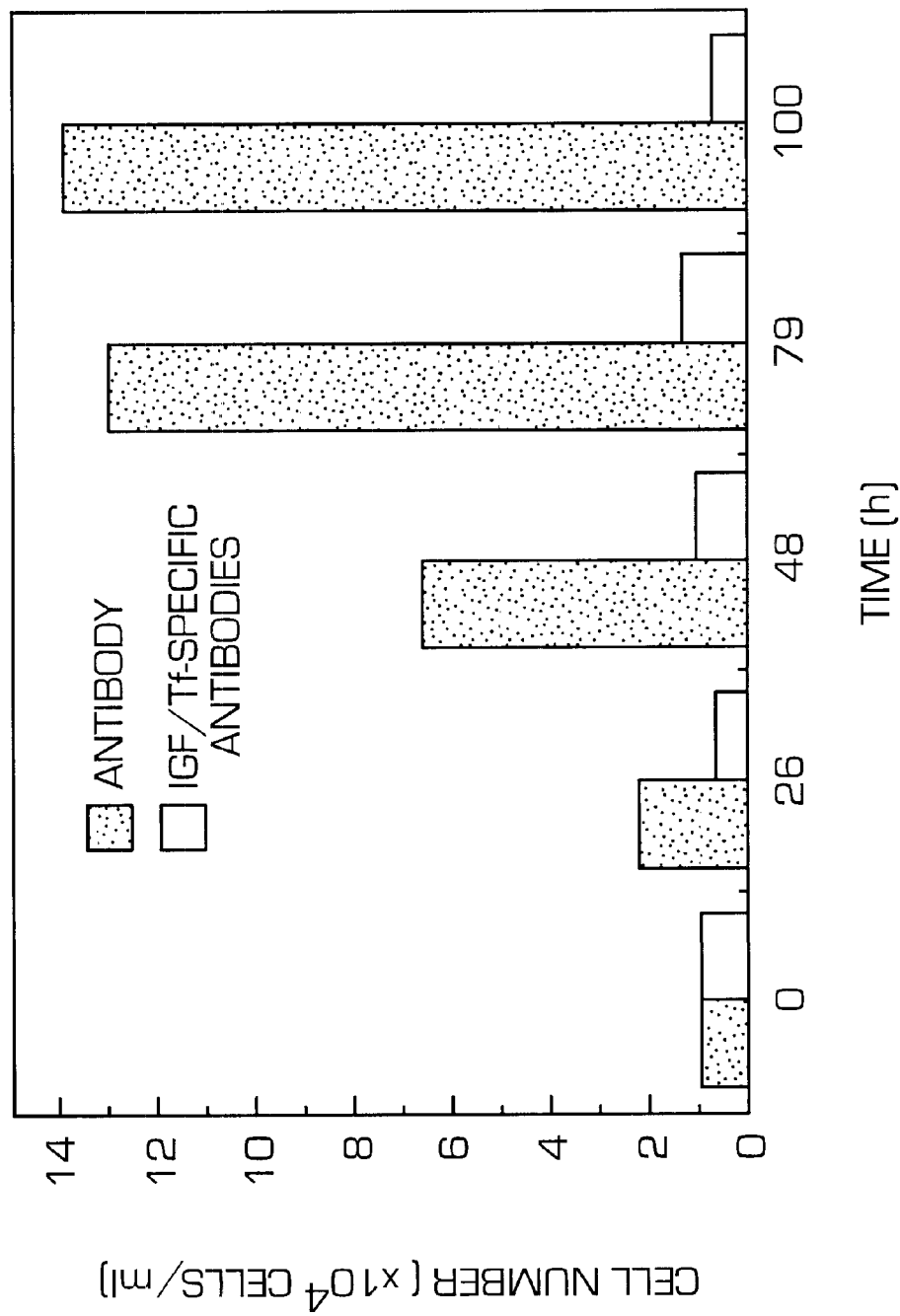

SEQUENCE LISTING

<160> NUMBER OF SEQ ID NOS: 4

<210> SEQ ID NO 1
<211> LENGTH: 7
<212> TYPE: DNA
<213> ORGANISM: mammalian

<400> SEQUENCE: 1 accatga                                                                    7

<210> SEQ ID NO 2
<211> LENGTH: 7
<212> TYPE: DNA
<213> ORGANISM: mammalian

<400> SEQUENCE: 2 aagatga                                                                    7

```
<210> SEQ ID NO 3
<211> LENGTH: 18
<212> TYPE: DNA
<213> ORGANISM: mammalian

<400> SEQUENCE: 3
attgtgagcg ctcacaat                                                  18

<210> SEQ ID NO 4
<211> LENGTH: 5
<212> TYPE: DNA
<213> ORGANISM: mammalian

<400> SEQUENCE: 4 tataa                                                                 5
```

REGULATED AUTOCRINE GROWTH OF MAMMALIAN CELLS

This invention relates to methods of production of recombinant biopharmaceuticals and other desirable proteins, polypeptides and peptides using mammalian cell cultures. More particularly, the methods of the invention involve the use of specifically bioengineered mammalian cell lines for the production of complex proteins in low cost media. These cell lines have the acquired ability for autonomous and regulated growth in cheap, reproducible, fully-defined protein-free medium, with the cells supplying all of their own growth factor requirements.

Mammalian cells have become the host cells of choice for the production of many of the new biopharmaceuticals, specifically those recombinant proteins requiring complex post-translational modifications and folding which bacterial cells cannot carry out. The production costs of these cells are far higher than with bacterial cells, with the fermentation cost accounting for an estimated 30% of the total production costs. The need to use a serum source in the growth and often production phases of the fermentation, is one of the contributing factors to the high costs of the fermentation.

Removing the need for added serum or growth factors in the fermentation medium will reduce media costs considerably. In addition, media free of added serum or growth factors should also be free of any viral or other contaminants. Further, the purity of the expressed protein will be maximized thus minimizing the steps in purification stages and maximising the recovery yield. This will allow production of complex processed protein in mammalian cell hosts but with many of the cost advantages associated with bacterial cell hosts. Also, in future years, commercial and regulatory pressures may well dictate a requirement for such purity in the production of mammalian cell derived recombinant protein.

Furthermore, with the rising cost of serum due to more stringent testing, there is a great demand for the development of cell lines that can grow on fully defined media. Indeed, several methods have been developed for growth of cultured cells in serum-free medium (Branes & Sato, 1980), including CHO-K1 (Mendiaz, E., et al., 1986). Media claiming to sustain growth in the absence of serum are available commercially. These are based on the fact that the serum requirements by cells in culture can be replaced by a combination of growth factors which is unique for each cell type. It is still unclear whether any of these media can sustain growth indefinitely. More recently, CHO-K1 cells have been used for high level expression of protein in serum-free medium (Ogata, M., et al., 1993), but these cells were maintained with serum during the growth phase and growth factors were added to the serum-free medium during the production phase. Although this system offers increased ease of product recovery, other factors cited above as making protein/serum-free growth media desirable, including cost, are not satisfied by this approach.

Australian patent specification No. 22120/88 (Genentech, Inc.) describes an attempt at engineering CHO cells to grow autonomously in protein-free medium. It is unclear whether these cells, which carry genes encoding insulin, transferrin and a desired protein product, are capable of continuously growing in the absence of serum. It is also unclear whether these cells are capable of expressing the desired protein product at satisfactory levels. Further, if cells such as CHO cells are engineered to produce growth factors in a constitutive fashion, then the mitogenic agents causing cell division would be present all the time and uncontrolled growth of the cells would result. Thus, in fermentation situations, it would be expected that cell numbers would increase in an uncontrolled fashion, causing in the case of attached cell cultures, multilayering of the cells and in the case of cells self-immobilised or growing as flocs, containing division resulting in cells in the centre of the flocs becoming anaeroic and necrotic. In the case of suspension cultures, it would be expected that cell densities would increase as would toxic metabolic byproducts having a negative effect on the viability and metabolism of the cells and the culture.

Thus the present inventors have now identified and developed a method of producing recombinant proteins utilising mammalian cell lines engineered for autonomous and regulated growth in low cost, protein/serum-free media.

In a first aspect, the present invention provides a method for producing a desired recombinant protein, polypeptide or peptide comprising the step of:
culturing a mammalian host cell in culture medium, wherein said host cell includes:
(i) at least one introduced DNA sequence encoding the desired protein polypeptide or peptide expressibly linked to a first inducible promoter sequence,
(ii) at least one introduced DNA sequence encoding a protein, polypeptide and/or peptide factor(s) required for growth of the host cell in said culture medium expressibly linked to a promoter sequence, the expression of which is regulated by a repressor binding region, and
(iii) at least one DNA sequence encoding a repressor molecule which binds to the repressor binding region, expressibly linked to a second inducible promoter sequence, wherein the first and second inducible promoter sequence(s) may be the same or different.

The invention enables the use of low cost, protein/serum-free medium by utilising a host cell which is able to produce the protein, polypeptide and/or peptide growth factor(s) required for its growth in such medium. The culture medium used in the method of the method of the invention is, therefore, preferably serum-free or otherwise free of protein, polypeptide and/or peptide growth factor(s) necessary for the growth of the particular host cell type. However, methods wherein the culture medium includes one or more of the required growth factor(s) and the host cell itself expresses one or more of the same and/or other required growth factor(s), is also to be regarded as falling within the scope of the invention.

By expressibly linking the DNA sequence(s) encoding the protein, polypeptide and/or peptide factor(s) required for growth of the host cell of a regulated promoter, the expression of the protein, polypeptide and/or peptide growth factor(s) can be controllably regulated so that production of the factor(s0 may be limited only to the stage of culturing where growth is required. Controllable regulation may be achieved by including a transcription-regulatory sequence (e.g., a repressor binding region such as from the lac repressor/operator system as modified for mammals. Hu and Davidson, 1987, and Kozak, 1986). Such transcription regulatory sequence(s) may be located at any location where it can exert a regulatory effect on expression from the second promoter. For example, the transcription regulatory sequence(s) may be located between the TATAA bus and the transcription start site or, alternatively, between the transcription start site and the AUG start codon.

Accordingly, the method of culturing may comprise a firs stage of culturing to a desired cell confluence and a second stage of culturing in the presence of the repressor. However, since the host cell further includes a DNA sequence encoding the repressor, the expression of which is regulated by an inducible promoter sequence, it is preferred that the method of culturing comprises a first stage of culturing to a desired cell confluence and a second stage of culturing in the presence of an inducer of second inducible promoter. Thus, the inducer may be added or applied to the host cell culture, thereby causing the expression of repressor and subsequent down regulation of growth factor(s) production.

It is also especially preferred to control the expression of the desired recombinant protein or peptide by the use of the same inducible promoter at that used to control the expression of the repressor. In this way, adding or applying inducer will cause the downregulation of growth factor(s) production and simultaneous expression of the desired protein or peptide. This enables an efficient method, which does not require changing the medium, wherein the host cell culture grows with minimal protein production, and then cell growth is minimised whilst protein production occurs. The effective separation of the growth and protein production phases may also be desirable if special ingredients (e.g., different sugars, etc.) were to be preferentially incorporated into the product.

Alternatively, the use of different inducible promoters may allow for fine control of relative expression levels.

The promoter expressibly linked to the at least one introduced DNA sequence encoding a protein, polypeptide and/or peptide factor(s) required for growth of the host cell, is preferably a constitutive promoter (such as the CMW and SV40 promoters) including a repressor binding region.

The mammalian host cell may be any of those commonly used in the art for expressing recombinant proteins or peptides. For example, the host cell may be a Chinese Hamster Ovary (CHO) cell such as CHO-K1.

The introduced DNA sequence(s) may be present on plasmids or otherwise integrated into the host cell chromosomes (e.g. by homologous recombination).

The DNA sequence(s) encoding the protein, polypeptide and/or peptide factor(s) required for growth of the host cell, may be selected from DNA sequences encoding insulin, modified insulins (e.g. to improve stability—see, for example, Brems, D. N. et al., 1992) insulin-like growth factors (e.g. IGF-1), transferrin, platelet derived growth factor (PDGF), cytokines, mitogenic proteases such as Trypsin. Thrombin and Cathepsin I, other growth factors and mixtures thereof. Where the host cell is CHO it is preferably that the host cell includes DNA sequences encoding insulin or insulin-like growth factors, and transferrin.

In a second aspect, the invention provides a host cell for use in the method according to the first aspect, wherein the host cell includes:

(i) at least one introduced DNA sequence encoding a desired protein, polypeptide or peptide expressibly linked to a first inducible promoter sequence.

(ii) at least one introduced DNA sequence encoding a protein polypeptide and/or peptide factor(s) required for growth of the host cell, expressibly linked to a promoter sequence, the expression of which is regulated by a repressor binding region, and (iii) at least one introduced DNA sequence encoding a repressor molecule which binds to the repressor binding region, expressibly linked to a second inducible promoter sequence.

wherein the first and second inducible promoter sequence(s) may be the same or different.

Host cells capable of autonomous and regulated growth in low cost protein/serum-free media may also be useful in other applications, e.g. in the production of viruses.

Thus, in a third aspect, the invention provides a method for the regulated growth of a mammalian host cell in a culture medium, comprising the step of:

culturing said mammalian host cell in said culture medium, wherein said host cell includes:

(i) at least one introduced DNA sequence encoding a protein polypeptide and/or peptide factor(s) required for growth of the host cell in said culture medium expressibly linked to a promoter sequence, the expression of which is regulated by a repressor binding region; and (ii) at least one DNA sequence encoding a repressor molecule which binds to the repressor binding region, expressibly linked to an inducible promoter sequence.

In a fourth aspect, the invention provides a host cell including:

(i) at least one introduced DNA sequence encoding a protein, polypeptide and/or peptide required for growth of the host cell in a protein/serum-free culture medium, expressibly linked to a promoter sequence, the expression of which is regulated by a repression binding region; and (ii) at least one introduced DNA sequence encoding a repressor molecule which binds to the repressor binding region, expressibly linked to an inducible promoter sequence.

Conveniently laboratories would be supplied with samples (e.g. frozen stock) of a cell line wherein the cells include DNA sequences encoding their growth factor requirements for protein/serum-free media. The samples may then be transformed to include DNA sequences encoding the desirable protein(s), polypeptide(s) and/or peptide(s) (or infected with virus), and then cultivated in a defined protein/serum-free medium to satisfactory numbers and with satisfactory growth rates without any added protein.

The invention will now be further described by way of the following non-limiting examples and with reference to the accompanying figures.

BRIEF DESCRIPTION OF THE FIGURES

FIG. 5A provides a graph showing transient expression of PGKlacOcat in CHO/M(1)2lacIN +/− metal and +/− IPTG. CHO/M(1)2lacIN cells were transiently transfected with PGKlacOcat, the cells were incubated for 48 hours post transfection in medium +/− metal and +/− IPTG. Levels of chloramphenicol transferase (cat) protein were measured in cell extracts. Levels of cat were expressed relative to uninduced levels set at 100%. Repression of <95% of the PKLlacOcat gene was observed in the presence of metal, and IPTG led to a derepression indicating that the observed representation was specific to the lac repressor.

FIG. 6 provides a Western blot analysis of metal induced Tf expression in CHO cells stably expressing the lacO-containing-Tf gene CMVlacOTf and the lac gene M(1)2lacINR.

A. Conditioned media from CHO/CMVlacOTf cell lines cultured for 24 hours in medium +/− metal (50 µm ZnCl$_2$) were analyzed for Tf expression by Western blot. Bulk cell line #2 and clonal line #1–19 were used. Tf was expressed in both lines. In bulk line #2, about 50% repression was observed in the presence of metal while very little repression was observed with the clonal line.

B. Cells from the two lines above were again examined for Tf expression by Western blot after 24 hours culture in medium +/− metal or IPTF (20 mM). The samples were done in triplicate. The levels of repression in the presence of metal in line #2 was similar to A, above. In line #1–19, the levels were too low to detect any repression. When ITPG was present, de-repression was observed in both cell lines + and − metal, i.e. the lacI gene was "leaky".

C. Twelve clones isolated from bulk line #2 were examined for Tf expression as above except that all cells were cultured in the presence of metal, IPTG was added to detect derepression. Derepression was observed in all the clones.

D. Clones 35 and 36 were analysed further for Tf expression in the presence or absence of metal and IPTG. The symbol ++ indicates the usual amount of metal used i.e. 50 µm ZnCl$_2$ and 1 µm CdCl$_2$. The symbol + indicates half of ++ levels. One, 2 to 10 µl of unsupplemented medium and 10 µl of supplemented medium was used. This allowed for a visual estimation of repression levels which were calculated to be >90% in medium + half strength metal and even greater in medium + full length metal.

Figure 7:
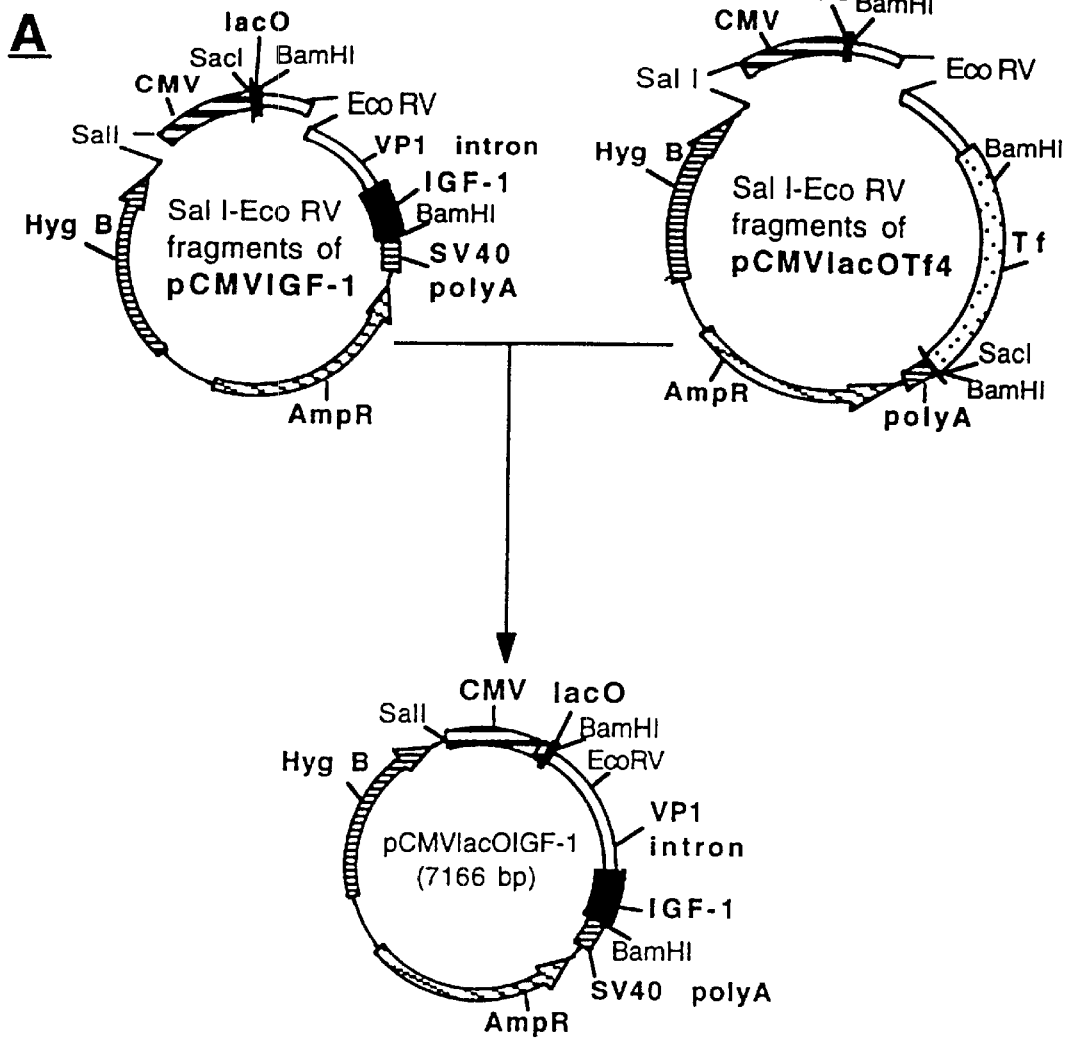

FIG. 7 shows the construction of the lacO-containing IGF-1 expressing plasmid pCMVlacOIGF.

A. The strategy used to make the pCMVlacOIGF construct is shown. A Sal I-Eco RV fragment was isolated from pCMVlacOTf and ligated in place of the respective fragment in pCMVIGF-1 to generate pCMVlacOIGF-1.

B. The expected restriction patterns, as analysed on an agarose gel, for the various restriction endonuclease digests used to isolate fragments for the above ligations and for identifying the generated construct are shown.

FIG. 8 provides an analysis of IGF-1 mRNA expression in lac-expressing CHO cells stably transfected with pCMVlacOIGF.

A. 10 µg of RNA from CHO cells transiently transfected with pCMWIacOIGF-1 and pPGKlacINR and cultured for 48 hours in medium +/− 20 mM IPTG was analysed by Northern blot for IGF-1 mRNA expression. The hybridized filter was exposed to a phosphorimager screen and the scanned image is shown. The levels were repressed in the presence of lac-expressing plasmid and derepressed in the presence of IPTG.

B. 10 µg of RNA from cell clones isolated from the above bulk transfected line was analysed for expression of IGF-1 and GAPDH mRNA as above. Various levels of IGF-1 mRNA was detected in the transfected cells but none in the CHO control.

C. Clone 7 was further analysed for IFG-1 and GAPDH mRNA expression as above. Cells were cultured for an initial 12 hours in medium +/1 metal (++=50 µM ZnCl$_2$ and 1 µM CdCl$_2$, +=25 µM ZnCl$_2$ and 0.5 µM CdCl$_2$) and +/− IPTG (20 mM). The levels of IGF-1 mRNA were quantified using the ImageQuant software and these are discussed in the text.

Figure 9:
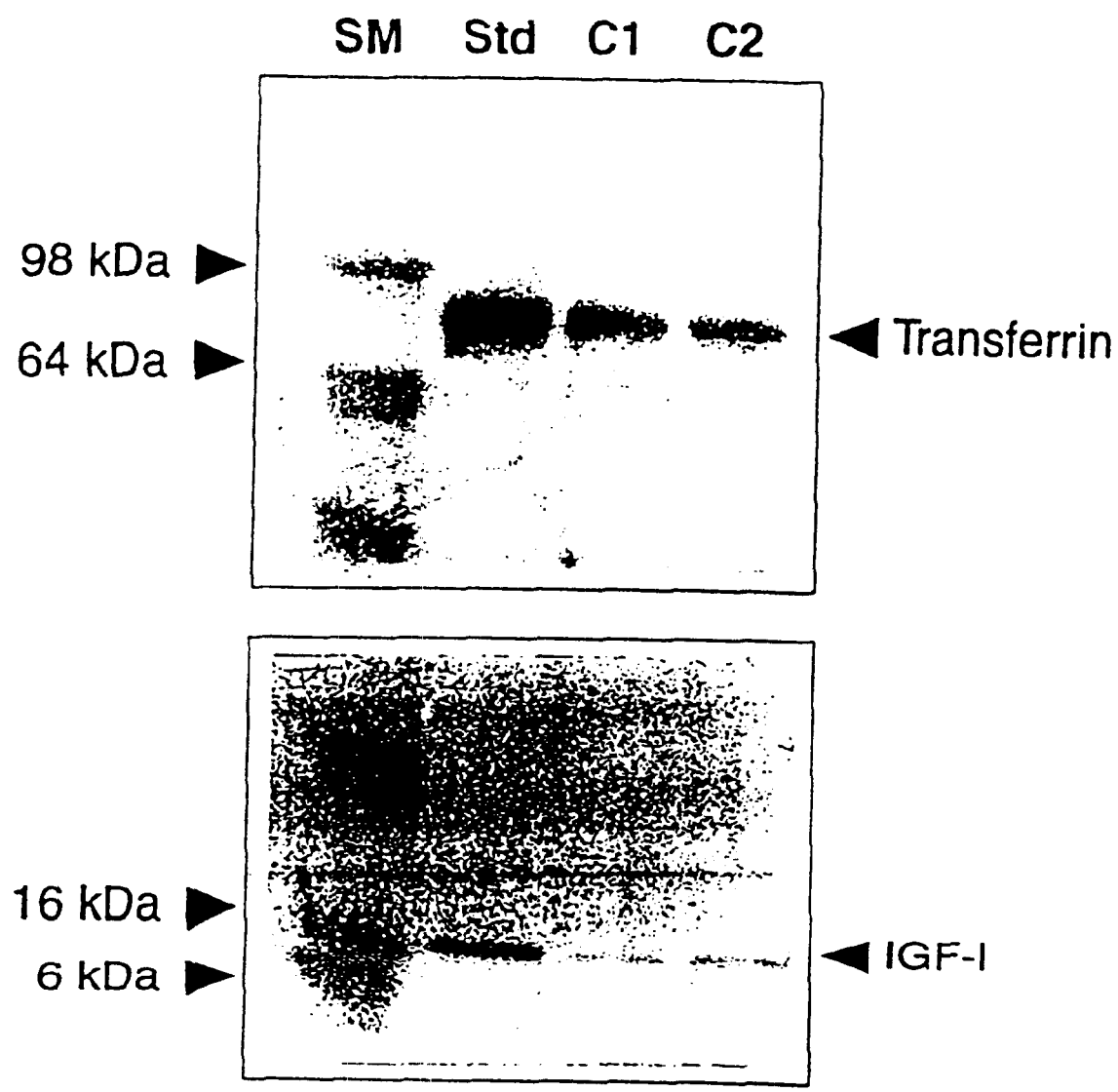

FIG. 9 provides a Western blot analysis of Super-CHO clones, C1 and C2. Conditioned medium of transfected CHO cells were analysed for the presence of correctly processed transferrin and IGF-1 by Western blot. Lane 1, 1 µg/ml transferrin standard (upper gel) and 10 µg/ml IGF-1 standard (lower gel); lane 2, conditioned medium from Super-CHO clone, C1 cells; lane 3, conditioned medium from Super-CHO clone, C2 cells.

Figure 10:
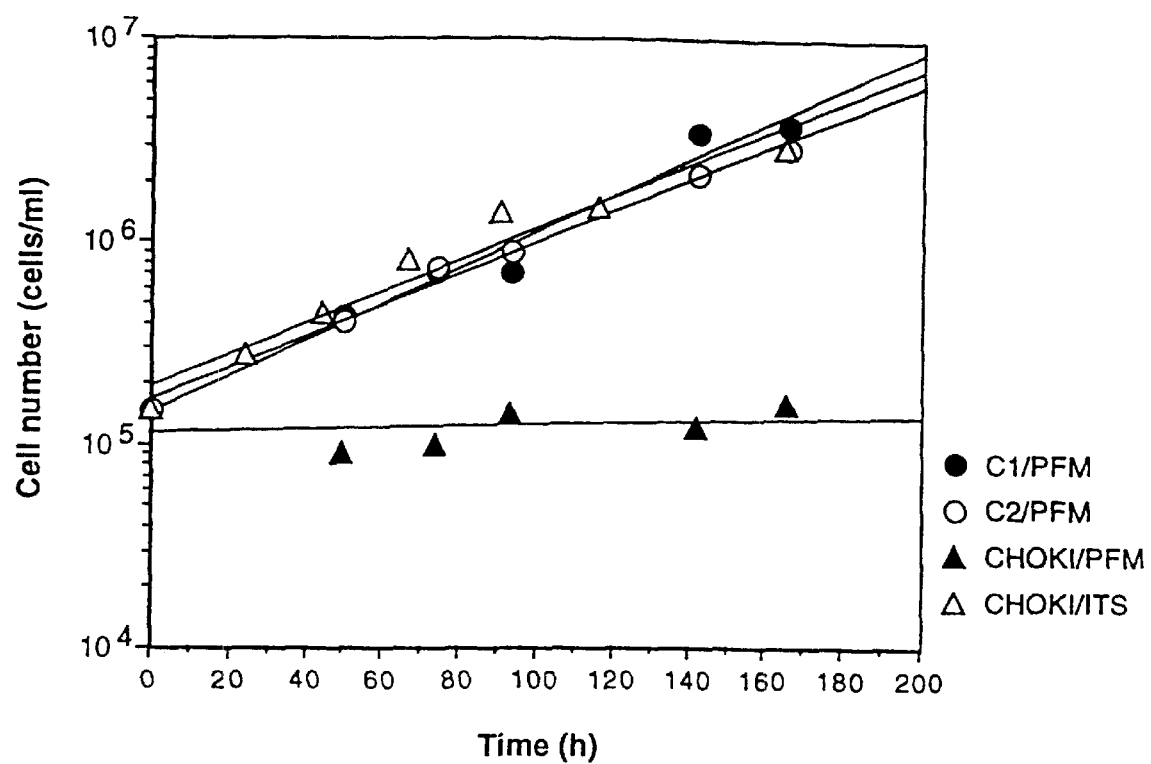

FIG. 10 shows the growth of 'Super-CHO' clones in protein-free medium Super-CHO cell clones C1 and C2 were inoculated into spinner flasks containing 100 ml of protein-free medium at a density of 1×10$^5$ cells/ml. Untransfected CHO cells were also inoculated into ITS and protein-free medium as positive and negative controls. Samples were taken each day for visual assessment and total cell number determination. The average of four cell counts for each time point is plotted against hours in culture.

FIG. 11 shows the effect of IGF-1, transferrin-specific antibodies on the growth of Super-CHO cells. Super-CHO cells. Super-CHO cell clone C1 was inoculated into a 30 mm tissue culture dish and incubated with protein-free medium containing 10 $\mu$l of IGF-1/transferrin-specific antisera or an irrelevant (WM 54) antibody. The number of viable cells were determined by trypan blue exclusion after 26, 48, 79 and 100 hours of culture. Triplicate plates were used for each time point and quadruplicate counts determined from each plate. The average cell number is plotted against time in culture.

Figure 12A:
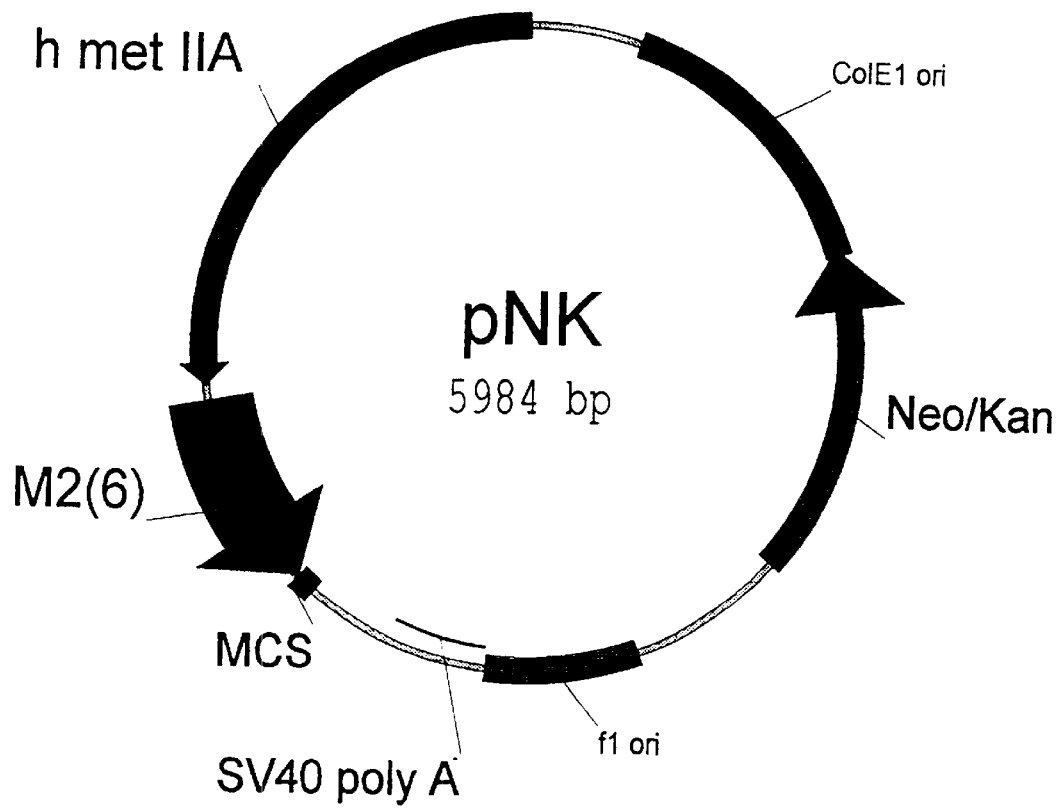

FIG. 12A shows, diagrammatically, the pNK construct. This construct was prepared from pBKCMV (Stratagene) and includes bacterial origins of replication (ColE1 ori and F1(−1) ori), a Neo/Kar marker expressed from the SV40 promoter, human metallothionein IIA gene (Kerin, M. & Richard, R., 1962) and the tightly regulated, highly inducible M(2)6 promoter (McNeall, J. et al., 1989) adjacent a multiple cloning site (MCS).

Figure 12B:
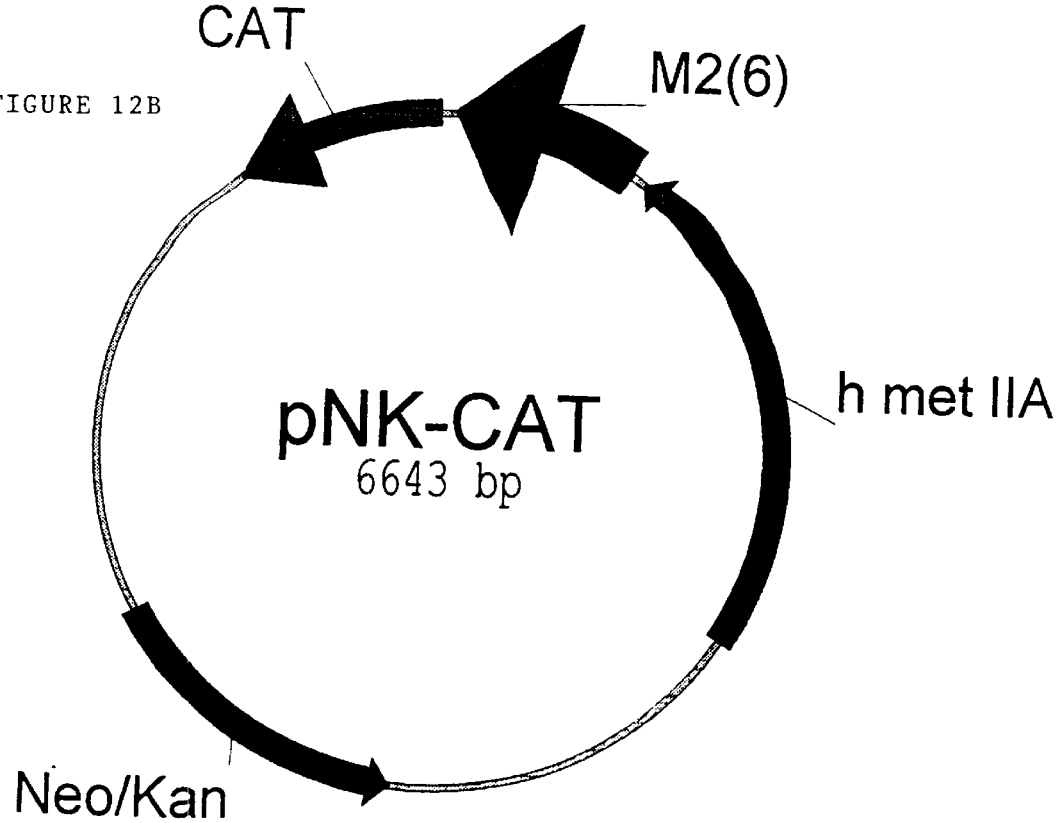

FIG. 12B shows, diagrammatically, the pNK-CAT construct, prepared by inserting a chloramphenicol transferase (CAT) marker into the MCS such that it is expressed from the M(2)6 promoter.

Figure 13:
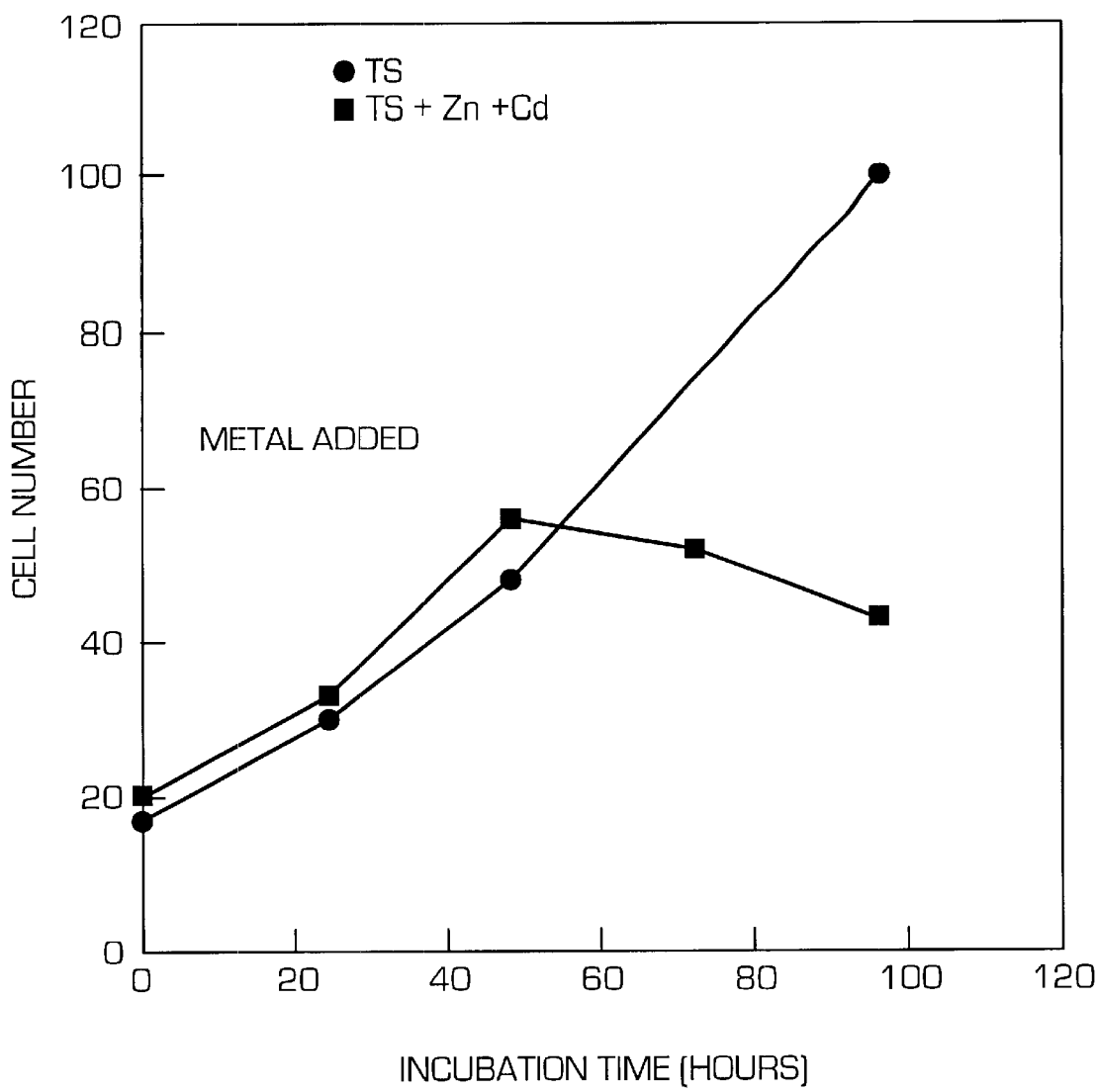

FIG. 13 shows, diagrammatically, the growth of CHO/CMVlacOIGF-1+M(1)lacINR on UNSWSF+TS medium. The control cells had no additions to the medium, to the other cells was added 50 $\mu$M ZnCl$_2$+1 $\mu$M CdCl$_2$ at 24 hours. Growth of the cells to which metal had been added plateaued whereas the control cells continued to grow.

Figure 14:
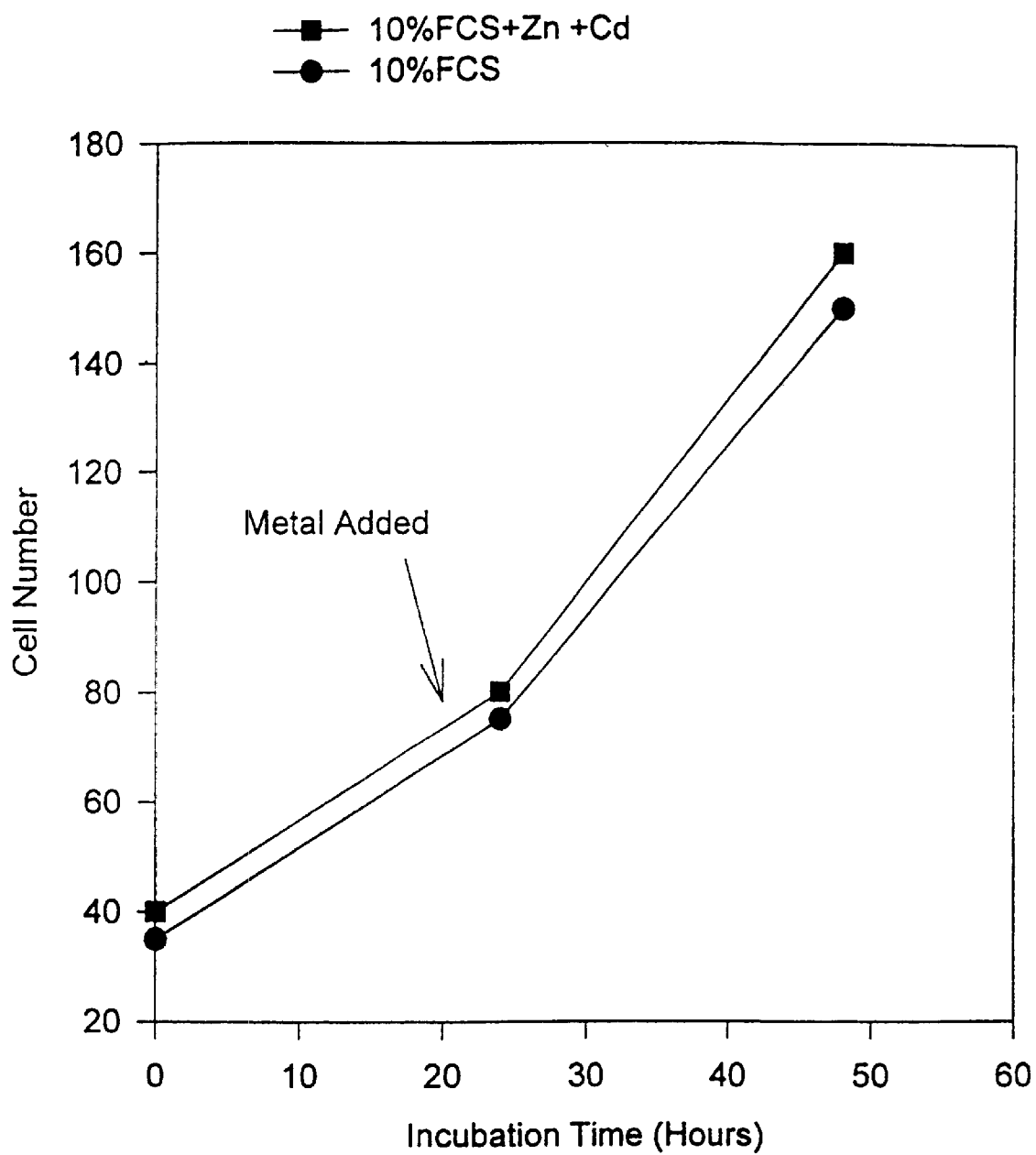

FIG. 14 shows, diagramatically, the growth of the cells shown in FIG. 12 on 10% FCS medium with and without the addition of 50 $\mu$M ZnCl$_2$ and 1 $\mu$M CdCl$_2$ at 24 hours. The growth of the cells was unaffected by the additional metal.

Figure 15:
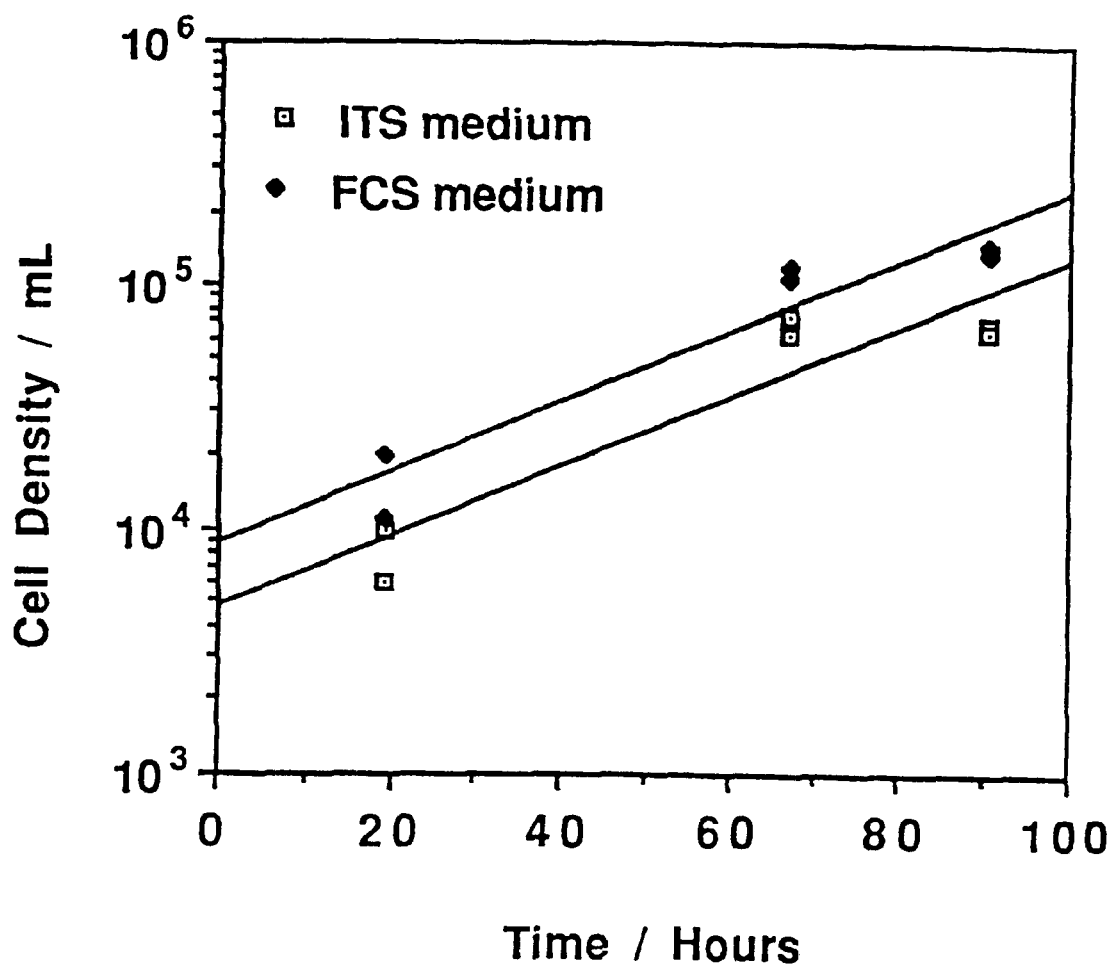

FIG. 15 shows, graphically, cell growth of CHO K1 in tissue culture flasks and compares it with cell growth achieved in foetal calf serum supplemented medium. Growth rates for the two columns ± standard errors are:

FCS Medium : doubling time=20.7±3.1 hours

ITS Medium : doubling time=21.0±4.0 hours

Figure 16:
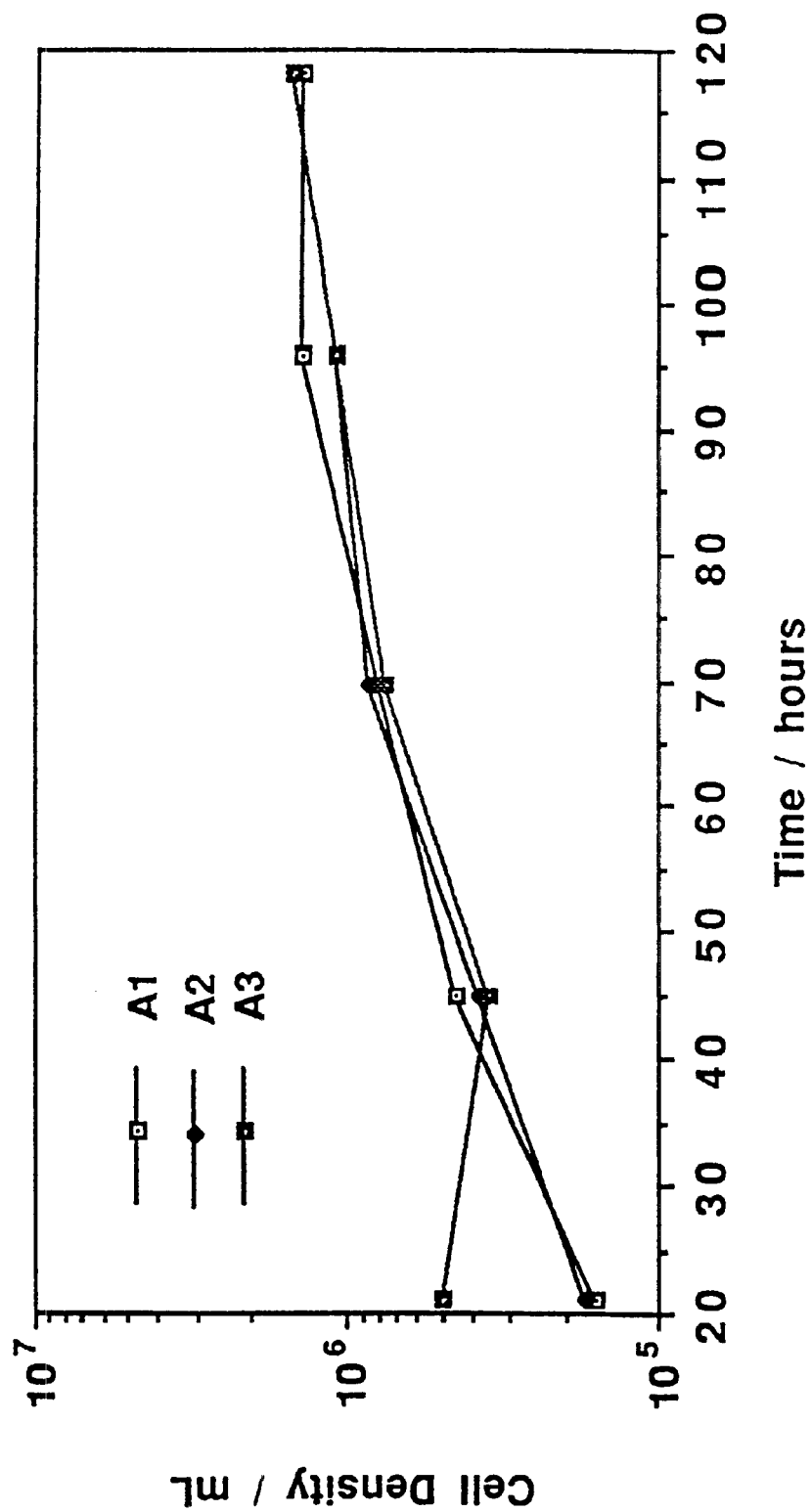

FIG. 16 shows, graphically, cell growth of CHO K1 on microcarriers in 100 ml stirred flasks. The flasks were duplicates (flask A and flask B). Growth rates for the two culture±standard errors for the first three points are:

Flask A : doubling time=18.9±3.2 hours

Flask B : doubling time=18.3±5.5 hours

EXAMPLES

Example 1

The expression of transferrin or IGF-1 in CHO cells

Work over the last few years has been conducted in order to gain an understanding of the growth requirements of CHO-K1 in serum free medium (Crowley, J., 1989, Gray, P. P. et al., 1990 and Bridges, M. PhD Thesis). Long term growth from liquid nitrogen to large scale may be obtained with insulin or insulin-like growth factor (IGF), transferrin and fibronectin or laminin as the only exogenous proteins. Selenium also needs to be added as a trace element. A defined serum-free (SF) medium was developed referred to as UNSWSF+ITS. Slight changes in growth characteristics of the CHO K1 cell line have occurred with different samples of CCL61 obtained over the years from American Type Culture Collection (ATCC). The current CHO K1 CCL61 stock obtained from ATCC in 1994 grows with a doubling time of around 17 hours in UNSWSF+TIS medium.

More recently it has been shown that IGF can be substituted for insulin for the growth of CHO K1 cell lines.

The coding sequences for the IGF1 and transferrin (Tf) genes, including the sequences for protein secretion, were isolated from a commercial human liver cDNA library (Clontech) using Polymerase Chain Reaction. Sequences 5' of the AUG start codon were modified to include an optimal translation initiation site (ACCATGA (SEQ ID NO:1) replacing AAGATGA (SEQ ID NO:2), Kozak, M., 1986).

The basic GF expression cassette, CMV-GF, contains the human cytomegalovirus (CMV) promoter from the major immediate early gene obtained from pCEF4 (Invitrogen), the VP1 intron from SV40 and the SV40 late polyadenylation/transcription termination signal from the commercial vector pSVL (Pharmacia) and the growth factor gene coding sequence.

The expression vector also contains a hygromycin resistance gene to confer on transfected cells a selectable phenotype, an ampicillin resistance gene and pUC origin of replication (bacterial sequences for in *E. coli*), all obtained from the plasmid pCEP4 (Invitrogen).

To generate a cell line that produces sufficient transferrin to support growth in transferrin-free UNSWSF medium+ Insulin, a recombinant transferrin expressing plasmid was constructed and introduced into CHO cells. Based on the high levels of exogenous transferrin required for serum-free (SF) growth (1 to 10,000 ng/ml), the construct was designed to give high expression levels. Firstly, the strong CMV promoter was used to ensure high transcriptional activity and, secondly, the construct was designed to maximise translatability by utilising a near optimal sequence for translation initiation around the AUG start site (Kozak, 1986). The effectiveness of the construct was subsequently tested in a transfected CHO cell culture by quantifying Tf mRNA and protein levels, and characterising growth of the cells in Tf-free medium.

Figure 1:
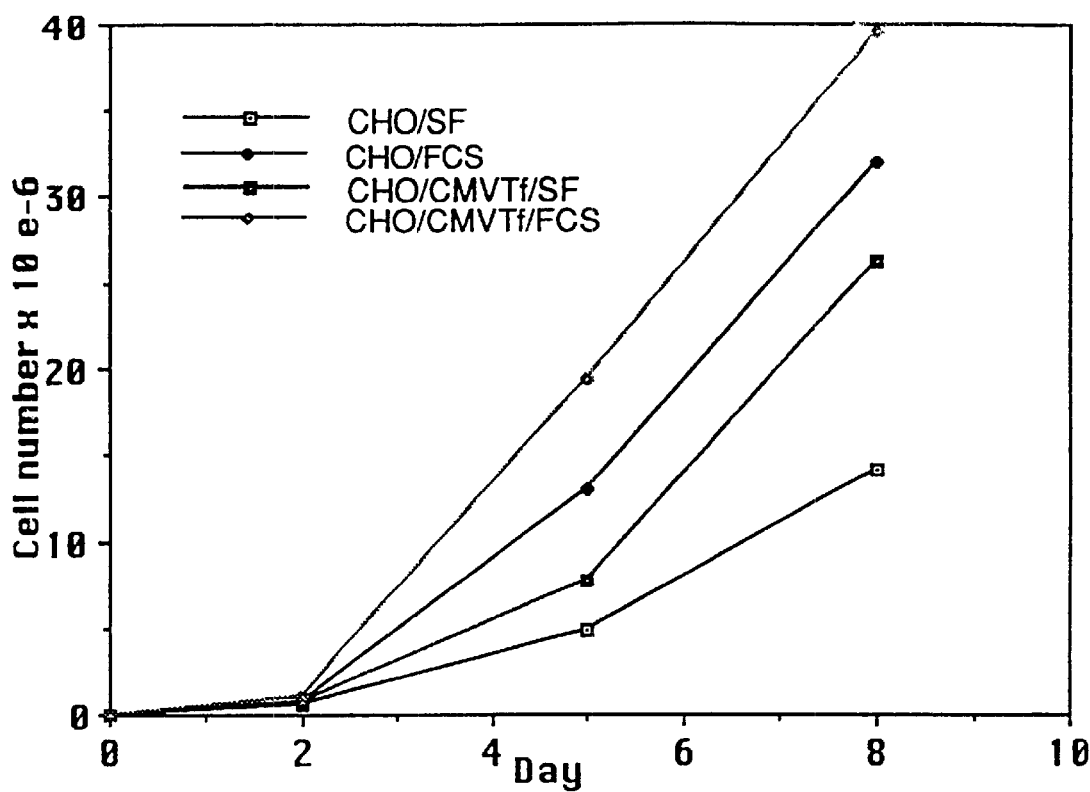
FIG. 1 shows graphically, the growth of CHO/CMVTf cells in UNSWSF medium IS. +5×10$^5$ CHO/CMVTf cells were plated in a 10-cm plate and grown in medium +10% foetal calf serum (FCS) for 24 hours. The medium was replaced with UNSWSF+IS medium (SF) or medium+10% FCS (FCS) and cells were allowed to grow for 8 days. The number of cells surviving after 2, 5 and 6 days was determined by counting the cells in a haemocytometer. Untransfected CHO cells were used as control. UNSWSF medium is a protein free medium made up of a mixture of DMEM/COONS F12 (Bridges, M., PhD Thesis, 1995) in a ratio of 1:1 +IS and sometimes +ITS refers to the presence of insulin, I, 10 mgs per liter; transferrin, T, 10 mgs per liter; Selenium, S, 2×10$^{-8}$; Molar, M sodium selenite.

The CMVTf gene was stably expressed in CHO cells by standard transfection into the cells followed by selection of transfected cells in medium containing 500 $\mu$g/ml of hygromycin B. Cells containing the hygromycin resistance gene also contained the recombinant gene. Those cells secreting high levels of Tf into the conditioned medium were identified by Western blot analysis. CHO/CMVTf cells secreted between 2 and 8 $\mu$g of Tf/$10^6$ cells/24 hours. These levels were sufficient to sustain growth in SF media+insulin+ selenium but no transferrin, the growth rate of these transfected cells being greatly improved when compared to that of untransfected CHO cells (FIG. 1). The growth rate seen for these cells was, however, less than that of the same cells grown in medium supplemented with 10% FCS.

Figure 2:
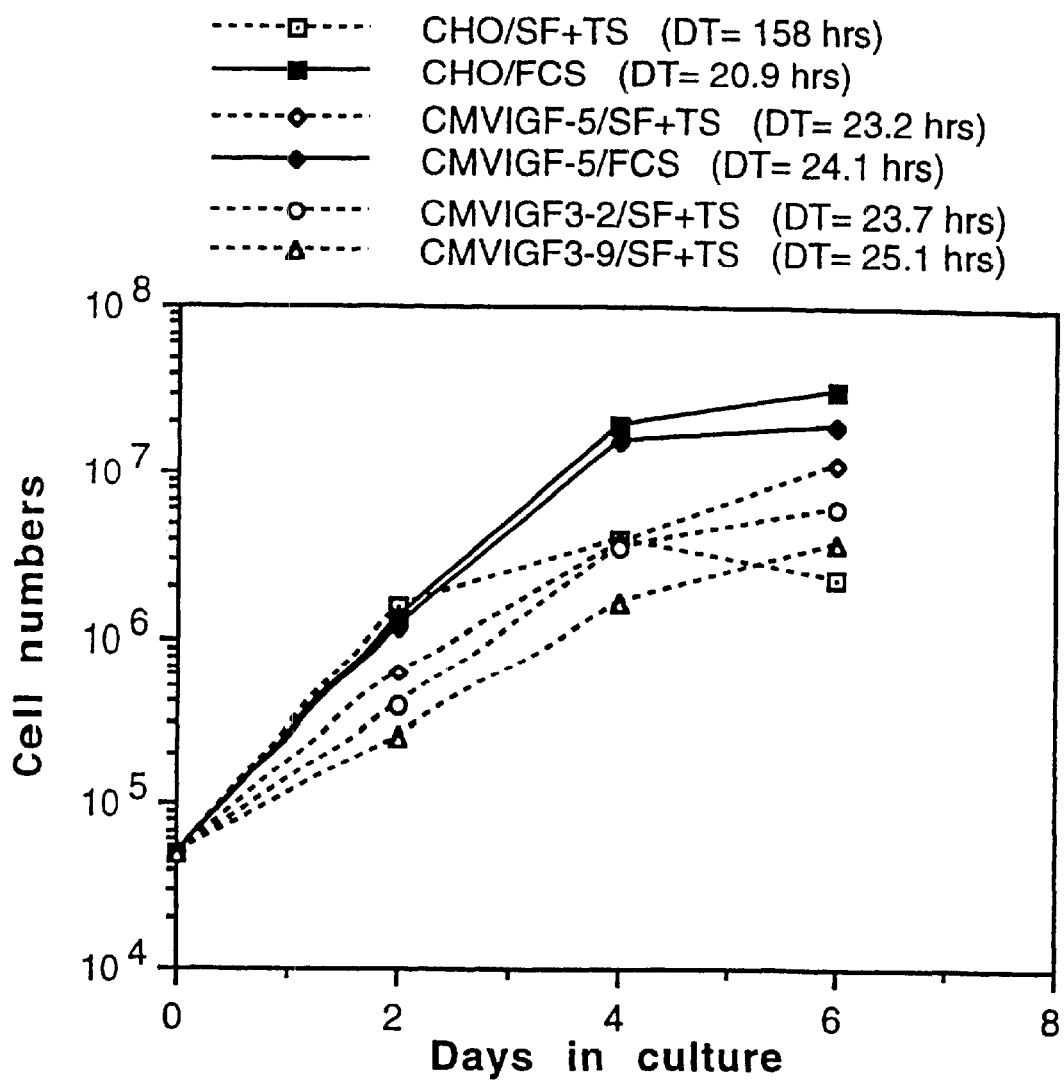
FIG. 2 shows, diagramatically, the growth of CHO/CMVIGF-1 cells in UNSWSF medium +TS. Cells from three different clonal isolates of CHO/CMVIGF-1 were plated at a density of 5×10$^4$ cells/10 cm plate and grown in medium +10% FCS for 24 hours. The medium was replaced with UNSW +IS medium (SF) or medium +10% FCS (FCS) and the cells were allowed to grow for 6 days; the number of viable cells were determined by trypan blue exclusion after 2, 4 and 6 days. Duplicate plates were used for each time point and the average number of cells are plotted against days in culture. Concentrations of insulin (I), transferrin (T) and selenium (S) were as for FIG. 1.

The CMVIGF-1 gene was similarly expressed in CHO cells. CHO/CMVIGF-1-cells secreting >200 ng/106 cells/24 hours showed greatly improved growth characteristics in SF media+transferrin+selenium compared to the parent line (FIG. 2). In FIG. 2, three clonal isolates of the cells were grown in UNSWSF and their growth compared to the same cells growing in FCS medium, and CHO-K1 growing in UNSWSF. The doubling times estimated for the cell lines are shown in Table 1.

TABLE 1

| Cell Line | Medium | Doubling Time (hours) |
|---|---|---|
| CHO/CMVIGF3-9 | UNSWSF + TS | 25.1 |
| CHO/CMVIGF3-2 | UNSWSF + TS | 23.7 |
| CHO/CMVIGF-5 | UNSWSF + TS | 23.2 |
| CHO-K1 | UNSWSF + TS | 15.8 |
| CHO-K1 | FCS | 20.9 |
| CHO/CMVIGF-5 | FCS | 24.1 |

The results indicate that the transfected cells were secreting sufficient quantities of biologically active IGF-1into the serum free, insulin-free medium to support their growth.

Example 2

Expression of the transferrin gene controlled by the SV promoter

Figure 3:
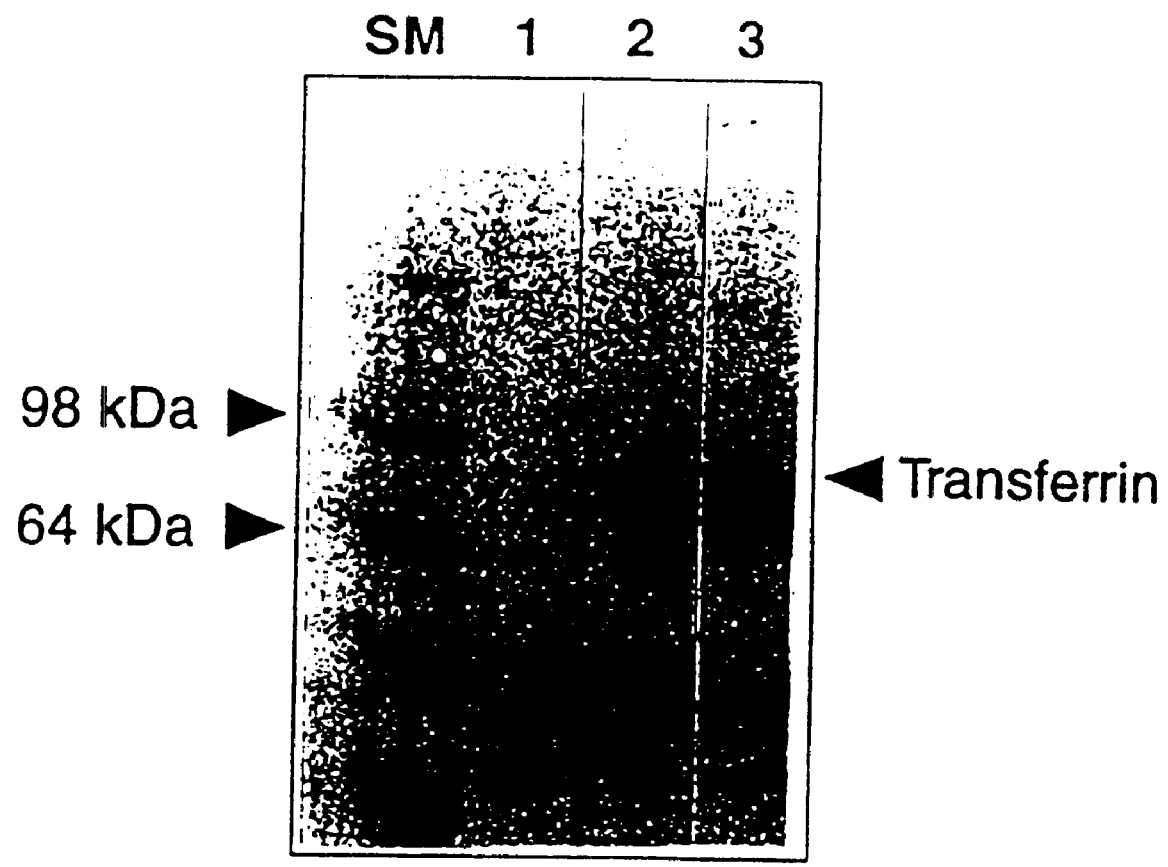
FIG. 3—provides a Western blot analysis of conditioned medium of CHOSVLTf cells carried out using a sheep anti-human transferrin primary and an alkaline phosphataseconjugated donkey anti-sheep secondary antibody. Lane 1, conditioned medium from untransfected patent CHO cells; lane 2, conditioned medium from bulk CHOSVLTf cells; lane 3, transferrin standard (1 µg/ml).

To demonstrate that the promoter used in driving the expression of transferrin was not critical, the cDNA coding for transferrin used in Example 1 was cloned into the Xho 1/Sc 1 sites of the vector pSVL to give rise to pSVL Tf. The SVL Tf gene was stably expressed in CHO cells by standard transfection into the cells (with pSV2Neo) (Southern, P. J. and Berg. P. 182) followed by selection in medium containing G418. FIG. 3 shows a Western blot of culture supernatants, showing that the cells were secreting correctly processed transferrin.

Figure 4A:
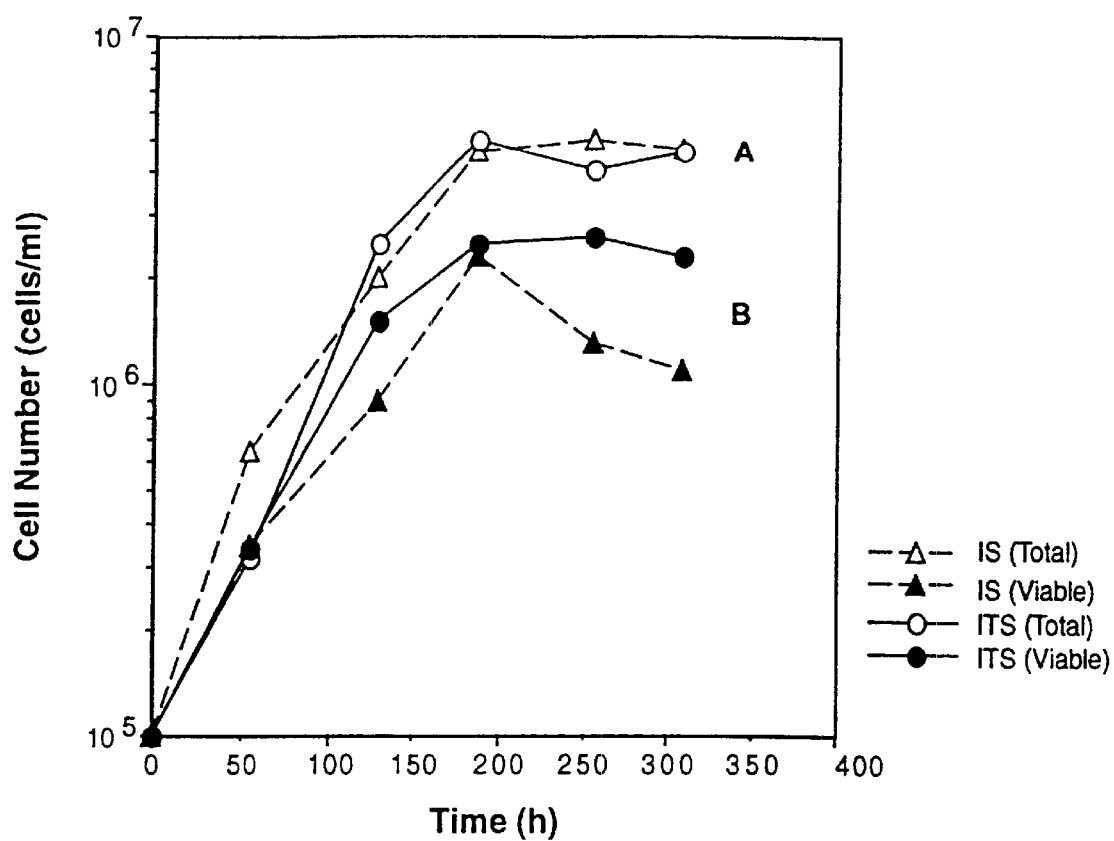
FIG. 4A shows graphically the effect of transferrin added to defined media on the long term growth of CHO-K1 cells in culture, CHO-K1 cells were inoculated into spinner flasks containing UNSWSF+IS medium or UNSWSF+ITS medium. The average of four total and viable cell counts for each time point was plotted against time in culture. CHO-K1 cells had a doubling time of 24 hours in UNSWSF+TS medium and 30 hours in UNSWSF+IS medium.
Figure 4B:
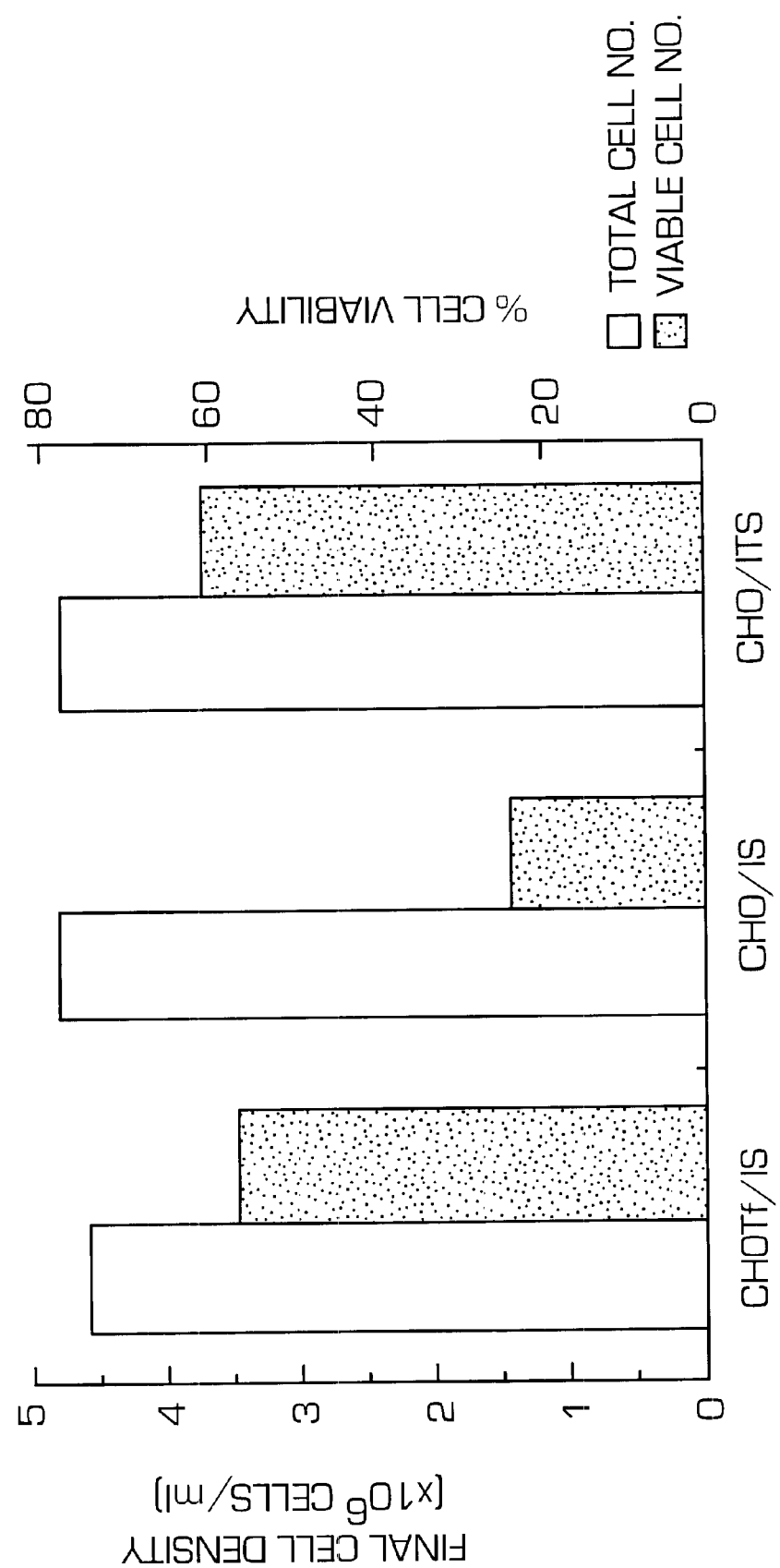
FIG. 4B shows the total and viable cell numbers after 250 hours growth in UNSWSF+IS medium. Lane 1, CHOSVLTf cells; lane 2, CHO-K1 cells; lane 3, CHO-K1 cells on UNSWSF+ITS medium.

FIG. 4A shows that the presence of transferrin in defined medium helped the long term growth and viability of CHO-K1 cells in culture. FIG. 4B shows the final cell numbers and percentage viability of CHOSVLTf cells maintained for greater than 10 days in IS medium. It can be seen from FIG. 4B that while the final cell densities for the three cell lines were similar, CHO-K1 growing on UNSWSF-ITS medium had a viability of 60%, similar to the CHOSVLTf cells expressing transferring, while the viability of the CHO-K1 cells growing on the UNSWSF+IS medium was only 20%. The data shows the importance of having the CHO cells secreting transferrin, particularly for long term stable growth and viability.

Example 3

Metal-inducible expression of lac repressor in CHO cells

The coding sequence for the *E. coli* lac repressor gene lacI has been modified for expression in mammalian cells (Hu and Davidson, 1987). It was further modified by incorporation of an optimal translation initiation signal (Kozak, M., 1986), and the nuclear localisation signal of the SV40 large T antigen into its N terminus for transport of the repressor protein into the nucleus (Hannan et al., 1993). The modified repressor gene, $lacI^N$, leads to 98% of the repressor protein being transported into the nucleus (Hannan et al., 1993).

An inducible $lacI^N$ gene was constructed. The expression cassette contains the modified human Metallothiouein IIA promoter, M(1)2 (McNeall, J. et al., 1989), the modified $lacI^N$ coding sequence described above, the SV40 VP1 intron and the SV40 late. polyadenylation and transcription termination signal described in Example 1.

Figure 5B:
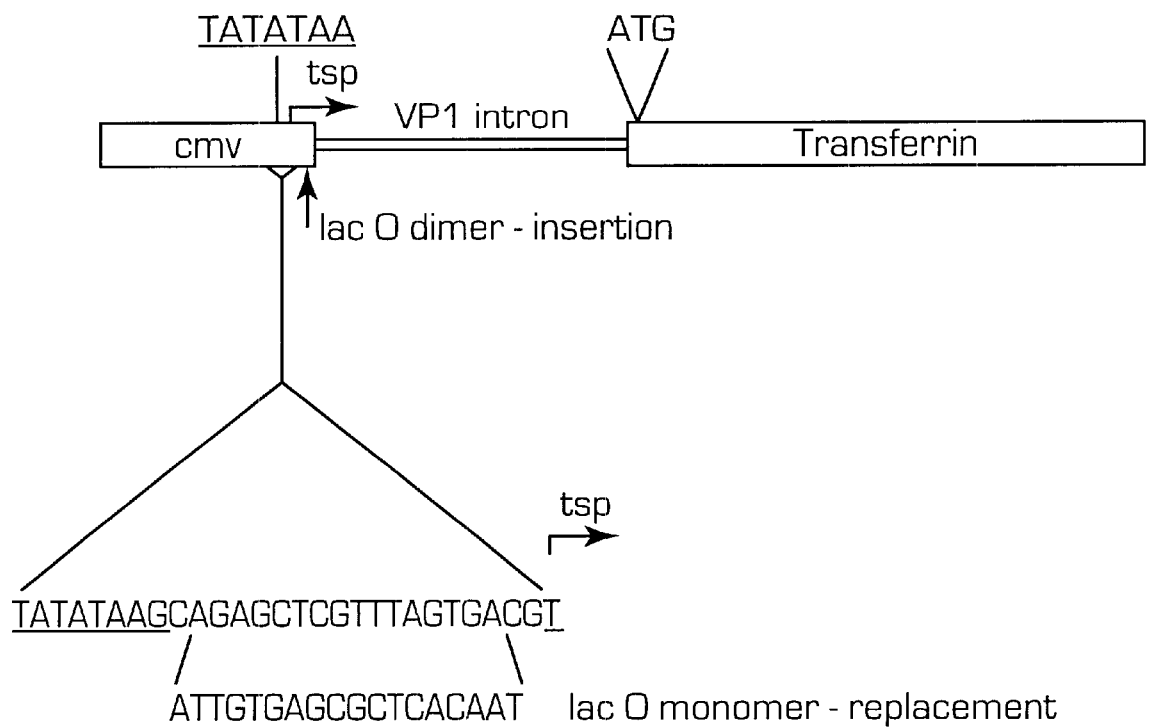
FIG. 5B shows, diagrammatically, the incorporation of lacO sequences in CMVTf to generate CMVlacOTF. The 18 base ideal lacO sequence was used to replace 18 bases in the CMV promoter between the TATAA box and transcription start point (tsp), and a dimer of that sequence was inserted into the restriction site Pme I between the tsp and the ATG start codon. The replacement was achieved by incorporating the LacO sequence in an oligonucleotide then used as a primer in a Polymerase Chain Reaction (PCR). The insertion of the lacO dimer was done by ligation of a restriction enzyme fragment from the plasmid pOP (Hannan, G., et al 1994) into the Pme I site of PCMVTf.

CHO cells were transfected using standard techniques with $M(1)2lacI^N$ and pSV2Neo. Cells were treated with 400 μg/ml G418 for 2 weeks and clonal cell lines resistant to G418 were selected. Clonal lines (designated CHO/R(5)4 and CHO/R(10)3) were obtained that produced low basal and high metal induced levels of repressor, as detected by Western blot. The repressor was shown to be biologically active by its ability to repress the lacO-containing plasmid PGKlacOcat (Hannan, G., et al., 1994) transiently introduced into the cells (FIG. 5A).

Example 4

The lac repressor/operator systems applied to CMVTf gene

An ideal lac operator sequence (ATTGTGAGCGCTCACAAT (SEQ ID NO:3)) based on the bacterial operator and rules for acceptable sites of insertion within a given promoter have been described (Hu & Davidson, 1987). The bacterial lac repressor has a high association constant for the ideal lac operator sequence which is a rate sequence with only three copies found in various mammalian genomes (Simons et al., 1984), thus offering good specificity of regulation of the target gene and minimal effect on the host genes (Simons et al., 1984).

Figure 5C:
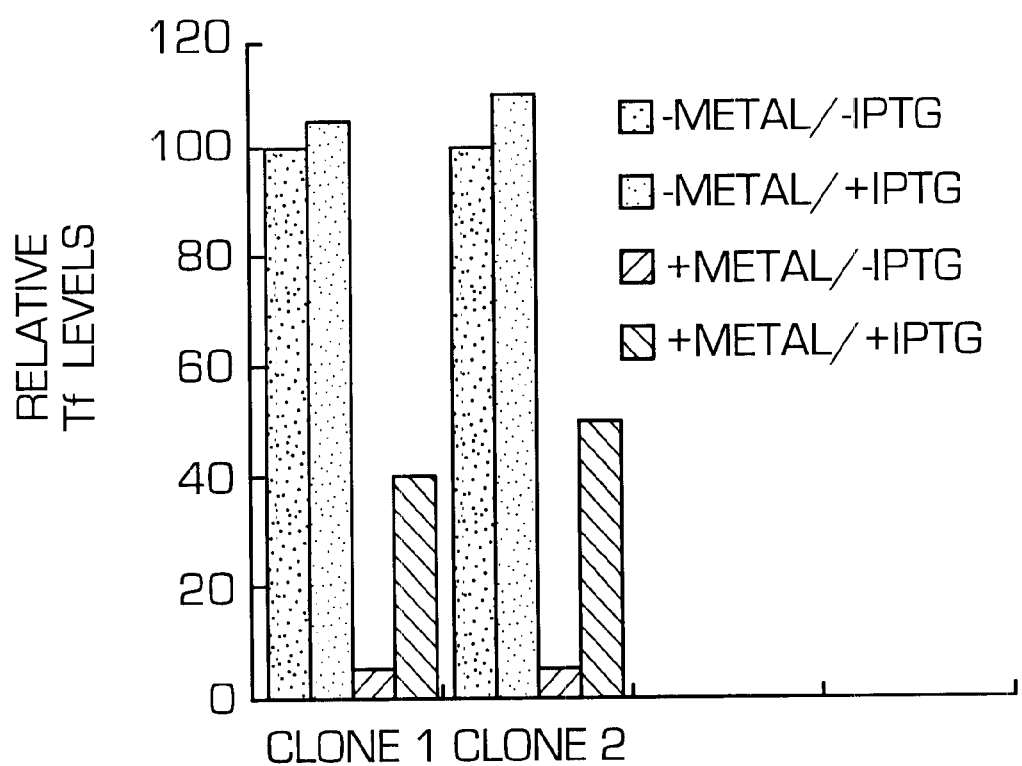
FIG. 5C provides a graph demonstrating the stable expression of CMVlacOTf in CHO/M(1)2lacIN. The plasmid pCMVlacOTf was transfected with CHO cells and stable transformants selected (labelled CHO/M(1)2 lacIN cells). Cells from 2 clonal lines were grown for 12 hours in medium +/− metal and +/− IPTF, fresh medium added and the conditioned medium collected after another 24 hours. Tf levels were estimated (visually) on a Western blot and are expressed relative to levels in the absence of metal and IPTG which was set at 100%. Metal induced repression levels of <90% was observed in both clones and IPTG relieved most of that repression indicating its specificity. Levels of IPTG used (20 mM) may have been sub-optimal thus explaining the incomplete derepression observed.

Lac operator sequences were inserted into the CMVTf gene to allow for repression by the lac repressor. One lac operator sequence (FIG. 5B) replaced promoter wild-type sequences between the TATAAA (SEQ ID NO:4) box and the transcription start point and the other two were inserted between the transcription start point and the AUG start codon. Stable expression of this new construct (CMVlacOTf) in CHO cells already containing a stable inducible lac repressor gene (see example 3) was significantly shut down when repressor protein was present (i.e. following metal induction) (FIG. 5C.

Example 5

Metal regulation of transferrin expression: stable expression and regulation of pCMVlacOTf into lacI expressing stable CHO clones CHO/R(5)4 and CHO/R(10)3

In order to ascertain whether the Tf gene within pCMV-lacOTf can be repressed when stably expressed in the lacI expression CHO clones CHO/R(5)4 and CHO/R(10)3, 10 μg of the plasmid was transfected into the cells by the $CaPO_4$ method (Chen, C., and Okayama, H., 1988). Transfected cells were selected in medium containing 500 μg/ml of Hygromycin B since the Tf gene carries the hygromycin resistance gene. Two batches of transfections, #1 and #2 were done on 2 separate days. 24 clones were isolated from transfected line CHO/R(5)4+Tf#1 at the time that foci of transfected cells started to appear. Conditioned medium from the bulk cell lines and the clonal lines were grown to sub-confluence n duplicate wells in a 6-well plate, metal was added to one of each of the duplicates and the medium was collected 24 hours later and analysed by Western blot for Tf content. The bulk line CHO/R(5)4+Tf#1 did not produce any Tf, however, clone 19 which was isolated from that line and the bulk line CHO/R(5)4+Tf#2 produced Tf. 50% repression was observed when the cells were treated with metal (FIG. 6).

The Tf expression pattern in the bulk line #2 and clone 19 was examined in more detail by seeding $2 \times 10^5$ cells in 60 mm plates (triplicate plates used per treatment), allowing cells to settle for 24 hr, adding fresh medium +/− metal and IPTG, and collecting the conditioned medium and harvesting cell extract (C/E) 72 hours later. The C/E was used to determine the protein levels in the plates. These levels were then used to normalise the volume of conditioned medium analysed in the Tf Western.

The ratio of Tf expression in the induced : Uninduced cells was used as a measure of repression. Similar repression levels to the above were detected but the levels were higher in the presence of IPTG for both induced and uninduced cells indicating that there was sufficient uninduced lac repressor present to repress the Tf gene (FIG. 6). Such a "leakiness" would be expected with the bulk line, but it should be possible to obtain a clonal line with a better balance of expression than that observed with clone 19. More clones needed to be isolated and screened for Tf production. Cells from the Tf-expressing bulk line #2 were plated at low density in 10 cm plates and 12 clones isolated by 'scraping' cells from isolated colonies as they appear (CHO/R(5)4+Tf-25 to 36).

Cells from the isolated clones above were grown in 6-well plates for 24 hours and the conditioned medium assayed for Tf content by Western blot (FIG. 6). Conditioned medium from all clones contained about 1 to 2 $\mu$g/ml of Tf (estimated from Tf stds, data not shown). Two clones were selected (CHO/R(5)4+Tf-35 and 36) and analysed further for Tf production in UNSWSF+IS medium +/– metal, +/– IPTG. Cells were seeded at 50% confluence levels with 6-well plates in medium +10% FCS and allowed to settle for 24 hrs. The medium was changed to UNSWSF+IS medium +/– metal, +/– IPTG. Two levels of metal were used, the normal level of 1 $\mu$M $CdCl_2$ and 50 $\mu$M of $ZnCl_2$ or half of that. IPTG was used at 20 mM final concentration. Fresh medium was added after 12 hours and conditioned medium collected 24 hrs later. The 12 hours of pre-treatment was done to remove any Tf secreted into the medium prior to metal induced repressor being produced and having its effect. 10 $\mu$l of supplemented conditioned medium, and 1, 2 and 10 $\mu$l of supplemented medium was analysed by Western blot. The varying amounts of the unsupplemented conditioned medium was used to allow for more accurate estimation of the repression levels (data not shown). There was no significant difference in Tf levels from the uninduced cells +/– IPTG, indicating that there was no basal repression. Metal induction led to repression of the Tf gene with levels reduced to about 10% relative to basal levels in both clones, halving the level of metal induction produced similar effects. IPTG relieved the repression thus confirming its specificity.

Clones 35 and 36 showed good repressor-regulated expression of the lacO-containing Tf gene, presumably due to optimal uninduced:induced repressor levels.

Example 6

Metal regulation of IGF-1 expression: regulation of IGF-1 expression from CMVlacOIGF-1 in a repressor positive CHO cell line To test for repressor-regulated expression of the MCVlacOIGF1 gene in a stable system, the plasmid was stably expressed in the optimal repressor positive CHO/M(1)2lacINR cell line R(5)4 in which the CMVlacOTf4 gene was successfully regulated. 10 $\mu$g of pCMVlacOIGF-1 (FIG. 7) was transfected into CHO/R(5)4 cells and hygromycin-resistant cells selected and pooled into the bulk cell line CHO/CMVIGF-1. In an effort to enrich for IGF-1 producing cells within the bulk cell line, the cells were grown in UNSWSF+TS medium for 2 weeks and the surviving cells pooled.

Cells from the bulk line were seeded at low density in 10 cm plates for clone isolation. 12 clones were isolated, expanded and screened for IGF-1 mRNA expression. Cytoplasmic RNA was extracted and 10 $\mu$g analysed for IGF-1-specific mRNA by Northern as above. The scanned image is shown in FIG. 8. The filter was stripped and re-probed for GAPDH mRNA.

The scanning results for the IGF-1 expressing clones are shown in FIG. 6. The 6 clones produced varying levels of IGF-1 mRNA. Clone 7 was selected for further analysis of IGF-1 mRNA expression in the presence and absence of metal. Cells were grown to sub-confluence in a 35 mm plate in medium +10% FCS +/– metal and +/– IPTG. Two levels of $ZnCl_2$+$CdCl_2$ was used as described in the brief description of FIG. 8. The medium was replaced with UNSWSF+ TS medium +/– metal of IPTG as above and the cells cultured for a further 24 hours. Cytoplasmic RNA was extracted for Northern analysis and the conditioned medium collected for Western analysis.

10 $\mu$g of RNA was analysed by Northern hybridization as above for IGF-1 mRNA expression. The hybridized membrane was exposed to a phosphorimager screen and the scanned image is shown in FIG. 8C. The membrane was stripped and re-probed for GAPDH mRNA as above. The mRNA levels were quantified (ImageQuant software) and IGF-1 levels normalised against GAPDH. Repression levels of 80% and 90% were observed in the presence of half strength and full strength metal levels respectively. IPTG led to a de-repression indicating the specificity of the repression.

Our results show that the expression of the CMVlacOIGF-1 gene stably transfected into lac-expressing CHO cells could be controlled by addition of metal to the medium. Since repression takes place at a transcriptional level and we did not observe any post-transcriptional control of our CMVIGF-1 gene in previous experiments, we can presume that the levels of IGF-1 produced by the cells above would correlate to the IGF-1 mRNA we observed.

Example 7

Cell lines expressing both transferring and IGF-1.

CHO-K1 was transfected with pSVLTf and pCMVIGF-1 by the usual procedures. Western blot analysis of the conditioned medium from bulk transfectants showed secretion of correctly processed transferrin and IGF-1 as indicated by the presence of two immunoreactive bands migrating at around 90 kDa and 7.6 kDa. Cell clones were isolated from the bulk by limiting dilution. Western blot analysis for two of these clones (SC1 and SC2) is shown in FIG. 9. Expression levels were estimated to be of the order of 750 ng of IGF-1 and 1000 ng of transferrin per $10^6$ cells per 24 hr.

To characterise the ability of SC1 and SC2 to grow in the serum and protein-free defined medium (UNSWSF) the clones were inoculated into spinner flasks containing micro-carriers. In the absence of any growth and attachment factors, both SC1 and SC2 grow well with doubling times of 18 and 21 hours respectively (FIG. 10). Under the same conditions, the untransfected parent cells grew extremely slowly with doubling times greater than 200 hours. The results show that sufficient IGF-1 and transferrin are being secreted to support autocrime growth under defined serum and protein-free conditions. The growth rates of the clones in UNSWSF were comparable to those exhibited by CHO-K1 in UNSWSF supplemented with ITS. Final cell densities of the SC1 and SC2 in UNSWSF were 4–5×$10^8$ cells per ml which was similar to the parent CHO-K1 in UNSWSF+ITF medium.

The ability of clones SC1 and SC2 to grow so well in the absence of any growth or attachment factors was unexpected since, in Example 10, it was shown that for the parent cell line CHO-K1 to be grown under fully defined conditions, it was necessary to coat the inoculum flask with fibronectin.

To confirm that the growth of the lines SC1 and SC2 is a direct result of the cells expressing transferrin and IGF-1, the clone SC1 was inoculated into 30 mm culture flasks with 10 μl of transferrin and IGF-1 specific antisera or an unrelated antibody (anti WM54). FIG. 11 shows that growth of SC1 was dramatically reduced in the presence of the anti IGF and transferrin antibodies. The results show that growth of the clone is a direct result of the expression of IGF-1 and transferrin.

A novel method was developed for the clones SC1 and SC2 which bypassed any need for propagation at any stage in the process in serum containing medium. Cells were directly inoculated into microcarrier culture from liquid nitrogen stocks. Growth rates and final cells densities were identical to those obtained when the cells were grown in a serum containing inoculum prior to being inoculated into microcarrier culture. The protocol was as follows:

(i) Liquid nitrogen stock;
(ii) Transfer to tube;
(iii) Centrifuge at 2000 rpm for 2 minutes;
(iv) Resuspend in protein-free medium (PFM);
(v) Viable cell count; and
(vi) Innoculate spinner flask.

These experiments were carried out with liquid nitrogen stocks containing serum. It is well known to those skilled in the art that it is possible to successfully freeze cells in a serum free medium (e.g., Yoshida and Takeuchi, 1991). Cells stocked in completely protein free medium were found to have a recovery rate of 50% compared with the recovery rate for cells stocked in serum of 80%.

Thus it has been shown that it is possible to grow cells according to the invention under totally protein-free, defined conditions from liquid nitrogen to stirred cultures.

Example 8

Regulated Autocrine Growth of CHO Cells

In this example, the autocrine growth of CHO cells expressing IGF-1 was regulated by the addition of metal. The metal turned on expression of the lac repressor which then bound to the lac operating binding site and turned off IGF-1 expression. CHO-K1 cells were transfected with plasmids containing pM(1)2lacINR, lac repressor under the control of the tightly regulated M(1)2 metallothionein promoter, pCMVlacOIGF-1, IGF under the control of the CMV promoter containing the lac operates binding site and pNK-CAT containing a whole metallothionein gene (Kerin, M & Richard, R. 1982). The pNK-CAT plasmid was constructed from pNK (FIG. 12).

Growth of the resulting transfectants was compared in the presence of serum (±addition of 50 μM $ZnCl_2$ and 1 μM $CdCl_2$) and on UNSWSF+TS medium.

The results are shown in FIGS. 13 and 14. It can be seen that the cells cultured in the presence of FCS showed no inhibition of growth upon the addition of the metal (FIG. 14), as the cells would be growing in the presence of insulin and the other mitogens present in serum as well as the IGF-1 produced by the cell line. The cells cultured in the TS medium (FIG. 13) grew well until the addition of metal which slowed cell growth allowing the cells to enter a stationary phase. The cells maintained in a stationary phase did not succumb to the toxic effects of the metal as evidenced by trypan blue exclusion stains. The combination of the inducible lac repressor system, the lac operator upstream of the IGF-1 coding sequence, was thus shown to be able to allow the regulatable autocrine growth of the CHO-K1 cells in that in the absence of metal, lac repressor was produced which turned off IGF-1 synthesis allowing the cells to enter a stationary phase.

In the cell lines developed in this study and capable of autocrine growth, IGF-1 was the mitogenic agent. The transferrin expressed in an autocrine fashion was necessary for the long term viability of the cells when they were allowed to grow in the serum and protein-free defined medium UNSWSF. Hence, in order to obtain regulated autocrine growth of the cells it is necessary to regulate IGF-1 expression; however, as shown in Example 5 it is also possible to regulate transferrin expression in the same fashion as IGF-1. This may be desirable in order to minimise growth factor(s) expression while the cells are expressing the desired recombinant protein, polypeptide or peptide.

Example 9

Expression of chloramphenicol transferase (CAT) from CHO-K1 with regulated expression of IGF-1.

It was shown that cells which could express IGF-1 in a regulated fashion could also express a recombinant protein. In particular it was shown that the regulatable promoter which could be used to turn on expression of the repressor protein and hence decrease IGF-1 expression could also be used to turn on expression of the desired recombinant protein. In the cells used in Example 8, CAT expression in pNK-CAT was under the control of the inducible by metal M(2)6 promoter. In this example, when after a period a cell growth, the same metal concentrations as used in Example 8 (50 mM $ZnCl_2$ and 1 mM $CdCl_2$) were added to the culture it was observed that the M(2)6 promoter switched on CAT expression.

Example 10

Culture conditions optimized for serum-free growth of CHO cells

CHO K1 cells may be stored in liquid nitrogen in a mixture of 90% medium and 10% DMSO. Upon thawing the cells may be grown in base medium +10 mg/L insulin +10 mg/L transferrin +2×10$^{-6}$ M selenium in a tissue culture flask coated with 400 ng/cm$^2$ fibronectin. At confluence the cells may be detached with cell dissociation solution (Sigma; USA) and used to re-inoculate new cultures under similar conditions in order to increase cell number. When a cell number is reached sufficient to allow a fermentor inoculation density of 1×10$^5$ cells/mL, the cells may be detached in a similar manner and used to inoculate a fermentor containing base medium +10 mg/L insulin +10 mg/L transferrin +2×10$^{-8}$ M selenium +10 mg/L cholesterol +2 g/L plurionic F68 (BASF, Germany)+3.0 g/L Dormacell 2.0% microcarriers (Pfiefer and Langhan, Germany). The cells will then grow until the microcarriers are confluent in the fermentor.

Base medium consists of a 1:1 mixture of DMEM and Coon's F12 media.

Results are provided at FIG. 15, which shows cell growth in tissue culture flasks and compares it with cell growth achieved in foetal calf serum supplemented medium. The growth rates for the two cultures ± standard errors are:

FCS medium: doubling time=20.7±3.1 hours

ITS medium: doubling time=21.0±4.0 hours

FIG. 16 shows cell growth on microcarriers in duplicate 100 mL stirred flasks. Growth rates for the two culture ± standard errors for the first three points are:

Flask A: doubling time=18.9±3.2 hours

Flask B: doubling time=18.3±5.5 hours

References

Barnes, D. and G. Sato. Methods for growth of cultured cells in serum-free medium. *Anal Biochem* 102 (1980): 255–270.

Bridges, M. PhD Thesis, The University of New South Wales, Sydney, 2052, Australia (1995).

Brems, D. N., Brown, P. L., Bryant C., Chance, R. E., Green, L. K., Long, H. B., Miller, A. A., Millican, R., Shields, J. E., and Frank, B. H. Improved insulin stability through amino acid substitution. *Protein Engineering* 5#6 (1992): 519–525.

Chen, C. and Okayama, H. Calcium phosphate Mediated Gene Transfer: a highly effective system for stably transforming cells with plasmid DNA. *Journal of Biotechniques* 6 (1988): 632–638.

Crowley, J., Gray, P. P. and Marsden, W. L. Production of human growth hormone using mammalian suspension culture. *Proc. 8th Australian Biotechnology Conference*, Sydney (1989): 407–410.

Gray, P. P., Crowley, J. M. and Marsden, W. L., Growth of a recombinant Chinese Hamster Ovary cell line and high level expression in protein free medium. *Trends in Animal Cell Culture Technology*, ed. Murakami, H., VCH I Kodansha, Tokyo (1990): 265–270.

Hannan, G. N., S. A. Lehnert, E. S. MacAvory, P. A. Jennings and P. L. Molloy. An engineered PGK promoter and lac operator-repressor system for the regulation of gene expression in mammalian cells. *Gene* 130 (1993): 233–9.

Hu, M. C. and N. Davidson. The inducible lac operator-repressor system is functional in mammalian cells. *Cell* 48 (1987): 555–66

Kelly, J. L., A. Sanchez, G. S. Brown, C. N. Chesterman and M. J. Sleigh. Accumulation of PDGF B and cell-binding forms of PDGF A in the extracellular matrix. *J. Cell Biol* 121 (1993): 1153–63.

Kerin, M & Richard, R. Human metallothionein genes—primary structure of the metallothionein II gene and a related processed gene, *Nature* 299 (1962): 797–802.

Kozak, M. Point Mutations Define a Sequence Flanking the AUG initiator Codon that Modulates Translation by Eukaryotic Ribosomes. *Cell* 44 (1986): 283–292.

Mendiaz, E., M. Mamounas, J. Moffett and E. Englesberg. A defined medium for and the effect of insulin on the growth, amino acid transport, and morphology of Chinese hamster ovary cells. CHO-K1 (CL 61) and the isolation of insulin "independent" mutants. *In Vitro Cell Dev Biol* 22 (1986): 66–74.

Mcneall, J., Sanchez, A. Gray, P., Chesterman, C. & Sleigh, M. Hyperinducible gene expression from ametallothionein promoter containing additional metal responsive elements. *Gene* 76 (1959) 81–88.

Ogata, M., K. Wakita, K. Kimura, Y. Marumoto, K. Ohi and S. Shimizu. High-Level Expression of Recombinant Human Soluble Thrombomodulin in Serum-Free Medium by CHO-K1 Cells. *Appl Microbiol Biotechnol* 38 (1993): 520–525.

Sadler, J. R., J. Sasmor and J. L. Betz. A perfectly symmetric lac operator binds the lac repressor very tightly. *Proc. Nat. Acad. Sci. USA* 80 (1983): 6785–6789.

Simons, A., D. Tils, B. von Wilcken-Bergmann and B. Muller-Hill. Possible ideal lac operator: *Escherical coli* lac operator-like sequences from eukaryotic genomes lack the central G-C pair. *Proc. Natl. Acad. Sci. USA* 81 (1984): 1624–6128.

Southern, P. J. and Berg. P. Transformation of Mammalian Cells to Antibiotic Resistance with Bacterial Gene under control of the SV40 Early Region Promoter, *Journal of Molecular and Applied Genetics* 1 (1982): 327–341.

Yoshida, T. and Takenuchi, M. 'Primary culture and cryopreservation of mouse ascites astrocytes under serum-free conditions', Cytotechnology, 5: 99–106, (1991).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of producing a desired protein, polypeptide or peptide, comprising the step of:
   culturing a mammalian host cell in culture medium under conditions to produce the desired protein, polypeptide or peptide, wherein said host cell includes:
   (i) at least one introduced DNA sequencing encoding the desired protein, polypeptide or peptide operably linked to a first inducible promoter sequence,
   (ii) at least one introduced DNA sequence encoding a protein, polypeptide and/or peptide factor(s) required for growth of the host cell in said culture medium operably linked to a promoter sequence, the expression of which is regulated by a repressor binding region; and
   (iii) at least one introduced DNA sequence encoding a repressor molecule which binds to the repressor binding region, operably linked to a second inducible promoter sequence,
   wherein the first and second inducible promoter sequence(s) may be the same or different, wherein said culturing comprises
   (i) a first stage of culturing said host cell to a desired cell confluence; and
   (ii) a second stage of culturing said host cell in the presence of an inducer of said first and second inducible promoter sequence(s),
   to produce the desired protein, polypeptide or peptide.

2. The method according to claim 1, wherein the first and second inducible promoter sequence(s) are the same.

3. A method according to claim 1 or 2, wherein the said repressor binding region is a lac operator sequence, and said at least one DNA sequence encoding a repressor molecule encodes a lac repressor.

4. A method according to claim 3, wherein the first and second inducible promoter sequence(s) is/are selected from the group consisting of the human metallothionein IIA promoter and the modified human metallothionein IIA promoters, M(1)2 and M(2)6.

5. A method according to claim 4, wherein the host cell further includes and expresses a DNA sequence encoding a metallothionein.

6. A method according to claim 5 additionally comprising the step of recovering the desired protein, polypeptide or peptide.

7. A host cell including:
   (i) at least one introduced DNA sequence encoding a desired protein, polypeptide or peptide operably linked to a first inducible promoter sequence;
   (ii) at least one introduced DNA sequence encoding a protein, polypeptide and/or peptide factor(s) required for growth of the host cell in a protein/serum-free culture medium, operably linked to a promoter sequence, the expression of which is regulated by a repressor binding region; and
   (III) at least one introduced DNA sequence encoding a repressor molecular which binds to a repressor binding region operably linked to a second inducible promoter sequence,
   wherein the first and second promoter sequence(s) may be the same or different.

8. A host cell according to claim 7, wherein the first and second inducible promoter sequence(s) are the same.

9. A host cell according to claim 7 or 8 wherein the said repressor binding region is a lac operator sequence, and said at least one DNA sequence encoding a repressor molecule encodes a lac repressor.

10. A host cell according to claim 9, wherein the first and second inducible promoter sequence(s) is/are selected from the group consisting of the human metallothionein IIA promoter and the modified human metallothionein IIA promoter, M(1)2 and M(2)6.

11. A host cell according to claim 10, wherein the host cell further includes and expresses a DNA sequence encoding a metallothionein.

* * * * *